US010047399B2

(12) United States Patent
Ting et al.

(10) Patent No.: US 10,047,399 B2
(45) Date of Patent: Aug. 14, 2018

(54) ABCA1 DOWNREGULATION IN PROSTATE CANCER

(71) Applicant: THE CLEVELAND CLINIC FOUNDATION, Cleveland, OH (US)

(72) Inventors: Angela H. Ting, Cleveland, OH (US); Byron H. Lee, Cleveland, OH (US)

(73) Assignee: THE CLEVELAND CLINIC FOUNDATION, Cleveland, OH (US)

( * ) Notice: Subject to any disclaimer, the term of this patent is extended or adjusted under 35 U.S.C. 154(b) by 107 days.

(21) Appl. No.: 14/148,241

(22) Filed: Jan. 6, 2014

(65) Prior Publication Data
US 2014/0193814 A1 Jul. 10, 2014

Related U.S. Application Data

(60) Provisional application No. 61/749,507, filed on Jan. 7, 2013.

(51) Int. Cl.
G01N 33/53 (2006.01)
C12Q 1/6886 (2018.01)
G01N 33/574 (2006.01)

(52) U.S. Cl.
CPC ..... *C12Q 1/6886* (2013.01); *G01N 33/57434* (2013.01); *C12Q 2600/118* (2013.01); *C12Q 2600/154* (2013.01); *C12Q 2600/158* (2013.01)

(58) Field of Classification Search
None
See application file for complete search history.

(56) References Cited

U.S. PATENT DOCUMENTS

| | | | |
|---|---|---|---|
| 3,654,090 A | 4/1972 | Wilhelmus et al. | |
| 3,850,752 A | 11/1974 | Schuurs et al. | |
| 4,016,043 A | 4/1977 | Schuurs et al. | |
| 4,671,958 A | 6/1987 | Rodwell et al. | |
| 4,741,900 A | 5/1988 | Alvarez et al. | |
| 4,867,973 A | 9/1989 | Goers et al. | |
| 6,555,323 B2 * | 4/2003 | Bamberger | G01N 33/92 435/4 |
| 7,901,942 B2 * | 3/2011 | Kamiie | G01N 30/7266 435/23 |

OTHER PUBLICATIONS

Wellington, C. L., et al., Laboratory Investigation, 82(3): 273-283, 2002.*
Fukuchi, J., et al. Cancer Research, 64: 7682-7685, 2004.*
Fitzgerald, M.L., et al. The Journal of Biological Chemistry, 276(18): 15135-15145, 2001.*
Sekine, Y., et al. Molecular Cancer Research, 8(9): 1284-1295, 2010.*
Addleman, M.D., "Cancer, Cholesterol and Cholestyramine", The New England Journal of Medicine, vol. 287, No. 20, p. 1047.
Browning et al., "Statins and Risk of Cancer: A Systematic Review and Metaanalysis", International Journal of Cancer, 2006, vol. 120, pp. 833-843.
Jacobs et al., "Cholesterol-Lowering Drugs and Advanced Prostate Cancer Incidence in a Large U.S. Cohort", Cancer Epidemiology, Biomarkers & Prevention, 2007, vol. 16, pp. 2213-2217.
Serre et al., "MBD-Isolated Genome Sequencing Provides a High-Throughput and Comprehensive Survey of DNA Methylation in the Human Genome", Nucleic Acids Research, 2010, vol. 38, No. 2, pp. 391-399.
Siperstein et al. "Deletion of the Cholesterol-Negative Feedback System in Liver Tumors", Cancer Research, 1964, vol. 24, pp. 1108-1115.
Yan et al., "Identification and Functional Analysis of Epigenetically Silenced MicoRNA's in Colorectal Cancer Cells", PLos One, 2011, vol. 6, Issue 6, pp. 1-11.
Lee et al., "Dysregulation of Cholesterol Homeostasis in Human Prostate Cancer Through Loss of ABCA1", American Association for Cancer Research, 2012, pp. 1-8.
Leon et al., "Alterations in Cholesterol Regulation Contribute to the Production of Intratumoral Androgens During Progression to Castration-Resistant Prostate Cancer in a Mouse Xenograft Model", The Prostate, 2010, vol. 70, pp. 390-400.
McCarty Jr. et al., "Use of a Monoclonal Anti-Estrogen Receptor Antibody in the Immunohistochemical Evaluation of Human Tumors", Cancer Research, 1986, vol. 46, pp. 4244s-4248s.
Mondul et al., "Association of Statin Use With Pathological Tumor Characteristics and Prostate Cancer Recurrence After Surgery", The Journal of Urology, 2011, vol. 185, pp. 1268-1273.
Mondul et al., "Statin Drugs, Serum Cholestrol, and Prostate Specific Antigen (PSA) in the National Health and Nutrition Examination Survey (NHANES) 2001-2004", Cancer Causes Control, 2010, vol. 21, pp. 671-678.
Murtola et al., "Cholesterol-Lowering Drugs and Prostate Cancer Risk: A Population-based Case-Control Study", Cancer Epidemiology, Biomarkers & Prevention, 2007, vol. 16, pp. 2226-2232.
Oh et al., "Cholesterol Level of Lipid Raft Microdomains Regulates Apoptotic Cell Death in Prostate Cancer Cells Through EGFR-Mediated Akt and ERK Signal Transduction", The Prostate, 2007, vol. 67, pp. 1061-1069.
Platz et al., "Men with Low Serum Cholesterol Have a Lower Risk of High-Grade Prostate Cancer in the Placebo Arm of the Prostate Cancer Prevention Trial", Cancer Epidemiology, Biomarkers & Prevention, 2009, vol. 18, pp. 2807-2813.

(Continued)

Primary Examiner — Sean E Aeder
(74) Attorney, Agent, or Firm — Tarolli, Sundheim, Covell & Tummino LLP

(57) ABSTRACT

A method of providing a prognosis or diagnosis of prostate cancer in a subject is described. The method includes obtaining a urine or prostate sample from the subject; determining the level of expression of ABCA1 in the sample; and comparing the level of expression of ABCA1 in the sample to the level of a control sample, wherein a decreased level of ABCA1 expression compared to the control indicates the subject has prostate cancer or a more severe form of prostate cancer. Methods of treating subjects identified as having prostate cancer, and kits for carrying out the method of prognosis or diagnosis are also described.

2 Claims, 5 Drawing Sheets

(56) References Cited

OTHER PUBLICATIONS

Pommier et al., "Liver X Receptor Activation Downregulates AKT Survival Signaling in Lipid Rafts and Induces Apoptosis of Prostate Cancer Cells", Oncogene, 2010, vol. 29, pp. 2712-2723.

Robinet et al., "A Simple and Sensitive Enzymatic Method for Cholesterol Quantification in Macrophages and Foam Cells", Journal of Lipid Research, 2010, vol. 51. pp. 3364-3369.

Schmitz et al., "Transcriptional Regulatory Networks in Lipid Metabolism Control ABCA1 Expression", Biochimica et Biophysica Acta, 2005, vol. 1735, pp. 1-19.

\* cited by examiner

SEQUENCE LISTING

<160> NUMBER OF SEQ ID NOS: 35

<210> SEQ ID NO 1
<211> LENGTH: 23
<212> TYPE: PRT
<213> ORGANISM: Homo sapiens

<400> SEQUENCE: 1

Cys Arg Leu Phe Ser Asp Ala Arg Arg Leu Leu Leu Tyr Ser Gln Lys
1               5                   10                  15

Asp Thr Ser Met Lys Asp Met
            20

<210> SEQ ID NO 2
<211> LENGTH: 28
<212> TYPE: DNA
<213> ORGANISM: Artificial Sequence
<220> FEATURE:
<223> OTHER INFORMATION: ABCA1 BSF1

<400> SEQUENCE: 2
ggttagaata gattagtttt ttaagaat                                      28

<210> SEQ ID NO 3
<211> LENGTH: 25
<212> TYPE: DNA
<213> ORGANISM: Artificial Sequence
<220> FEATURE:
<223> OTHER INFORMATION: ABCA1 BSR1

<400> SEQUENCE: 3
aactctaata accccaaaac tctac                                        25

<210> SEQ ID NO 4
<211> LENGTH: 25
<212> TYPE: DNA
<213> ORGANISM: Artificial Sequence
<220> FEATURE:
<223> OTHER INFORMATION: ABCA1 BSF2

<400> SEQUENCE: 4
atttaggagg ttgaggtagg agaat                                        25

<210> SEQ ID NO 5
<211> LENGTH: 25
<212> TYPE: DNA

```
<213> ORGANISM: Artificial Sequence
<220> FEATURE:
<223> OTHER INFORMATION: ABCA1 BSR2

<400> SEQUENCE: 5
aaataccaac actaaatctt cactc                                        25

<210> SEQ ID NO 6
<211> LENGTH: 24
<212> TYPE: DNA
<213> ORGANISM: Artificial Sequence
<220> FEATURE:
<223> OTHER INFORMATION: ABCA1 BSF3

<400> SEQUENCE: 6
gagggaggat tgggtatttt attt                                         24

<210> SEQ ID NO 7
<211> LENGTH: 26
<212> TYPE: DNA
<213> ORGANISM: Artificial Sequence
<220> FEATURE:
<223> OTHER INFORMATION: ABCA1 BSR3

<400> SEQUENCE: 7
ttcaacttat taaccaaact aatctc                                       26

<210> SEQ ID NO 8
<211> LENGTH: 25
<212> TYPE: DNA
<213> ORGANISM: Artificial Sequence
<220> FEATURE:
<223> OTHER INFORMATION: ABCA1 BSF4

<400> SEQUENCE: 8
gtagagtttt ggggttatta gagtt                                        25

<210> SEQ ID NO 9
<211> LENGTH: 26
<212> TYPE: DNA
<213> ORGANISM: Artificial Sequence
<220> FEATURE:
<223> OTHER INFORMATION: ABCA1 BSR4

<400> SEQUENCE: 9
aaaaacttat caaaaaataa aaaaaa                                       26

<210> SEQ ID NO 10
<211> LENGTH: 30
<212> TYPE: DNA
<213> ORGANISM: Artificial Sequence
<220> FEATURE:
<223> OTHER INFORMATION: ABCA1 BSF5

<400> SEQUENCE: 10 ggttttttgtt tatgtagttt agttatttag                                  30

<210> SEQ ID NO 11
<211> LENGTH: 26
<212> TYPE: DNA
<213> ORGANISM: Artificial Sequence
<220> FEATURE:
<223> OTHER INFORMATION: ABCA1 BSR5

<400> SEQUENCE: 11
aaccctaaaa cacctactat accctc                                       26
```

<210> SEQ ID NO 12
<211> LENGTH: 25
<212> TYPE: DNA
<213> ORGANISM: Artificial Sequence
<220> FEATURE:
<223> OTHER INFORMATION: ABCA1 BSF6

<400> SEQUENCE: 12
agggtatagt aggtgtttta gggtt                                    25

<210> SEQ ID NO 13
<211> LENGTH: 28
<212> TYPE: DNA
<213> ORGANISM: Artificial Sequence
<220> FEATURE:
<223> OTHER INFORMATION: ABCA1 BSR6

<400> SEQUENCE: 13
caaaatttaa aaaaaacaaa ttccacta                                 28

<210> SEQ ID NO 14
<211> LENGTH: 26
<212> TYPE: DNA
<213> ORGANISM: Artificial Sequence
<220> FEATURE:
<223> OTHER INFORMATION: ABCA1 BSF8

<400> SEQUENCE: 14
ttttttttat tttttgataa gttttt                                   26

<210> SEQ ID NO 15
<211> LENGTH: 29
<212> TYPE: DNA
<213> ORGANISM: Artificial Sequence
<220> FEATURE:
<223> OTHER INFORMATION: ABCA1 BSR8

<400> SEQUENCE: 15
ctaaataact aaactacata aacaaaaac                                29

<210> SEQ ID NO 16
<211> LENGTH: 26
<212> TYPE: DNA
<213> ORGANISM: Artificial Sequence
<220> FEATURE:
<223> OTHER INFORMATION: ABCA1 M F1

<400> SEQUENCE: 16
tattagagtt cgtattagga tatcgt                                   26

<210> SEQ ID NO 17
<211> LENGTH: 26
<212> TYPE: DNA
<213> ORGANISM: Artificial Sequence
<220> FEATURE:
<223> OTHER INFORMATION: ABCA1 M R1

<400> SEQUENCE: 17
cttaaacgtt attattttat ttcgaa                                   26

<210> SEQ ID NO 18
<211> LENGTH: 29
<212> TYPE: DNA
<213> ORGANISM: Artificial Sequence
<220> FEATURE:

<223> OTHER INFORMATION: ABCA1 U F1

<400> SEQUENCE: 18
ggttattaga gtttgtatta ggatattgt                                29

<210> SEQ ID NO 19
<211> LENGTH: 32
<212> TYPE: DNA
<213> ORGANISM: Artificial Sequence
<220> FEATURE:
<223> OTHER INFORMATION: ABCA1 U R1

<400> SEQUENCE: 19
ataacttact taaacattat tattttattt ca                            32

<210> SEQ ID NO 20
<211> LENGTH: 26
<212> TYPE: DNA
<213> ORGANISM: Artificial Sequence
<220> FEATURE:
<223> OTHER INFORMATION: ABCA1 M F2

<400> SEQUENCE: 20
ataaggagta aagcgttttg agaatc                                   26

<210> SEQ ID NO 21
<211> LENGTH: 26
<212> TYPE: DNA
<213> ORGANISM: Artificial Sequence
<220> FEATURE:
<223> OTHER INFORMATION: ABCA1 M R2

<400> SEQUENCE: 21
tacgaacgaa ataaataaa accgaa                                    26

<210> SEQ ID NO 22
<211> LENGTH: 26
<212> TYPE: DNA
<213> ORGANISM: Artificial Sequence
<220> FEATURE:
<223> OTHER INFORMATION: ABCA1 U F2

<400> SEQUENCE: 22
aaggagtaaa gtgttttgag aattgg                                   26

<210> SEQ ID NO 23
<211> LENGTH: 26
<212> TYPE: DNA
<213> ORGANISM: Artificial Sequence
<220> FEATURE:
<223> OTHER INFORMATION: ABCA1 U R2

<400> SEQUENCE: 23
tacaaacaaa ataaataaa accaaa                                    26

<210> SEQ ID NO 24
<211> LENGTH: 21
<212> TYPE: DNA
<213> ORGANISM: Artificial Sequence
<220> FEATURE:
<223> OTHER INFORMATION: ABCA1 M F3

<400> SEQUENCE: 24
tagaaagtac gtggagtcgg g                                        21

<210> SEQ ID NO 25
<211> LENGTH: 24
<212> TYPE: DNA
<213> ORGANISM: Artificial Sequence
<220> FEATURE:
<223> OTHER INFORMATION: ABCA1 M R3

<400> SEQUENCE: 25
aaaaaaaaaa acgcaaaccg cgaa         24

<210> SEQ ID NO 26
<211> LENGTH: 22
<212> TYPE: DNA
<213> ORGANISM: Artificial Sequence
<220> FEATURE:
<223> OTHER INFORMATION: ABCA1 U F3

<400> SEQUENCE: 26
tagaaagtat gtggagttgg gg           22

<210> SEQ ID NO 27
<211> LENGTH: 24
<212> TYPE: DNA
<213> ORGANISM: Artificial Sequence
<220> FEATURE:
<223> OTHER INFORMATION: ABCA1 U R3

<400> SEQUENCE: 27
acacaaacca caaaccctaa aaca         24

<210> SEQ ID NO 28
<211> LENGTH: 20
<212> TYPE: DNA
<213> ORGANISM: Artificial Sequence
<220> FEATURE:
<223> OTHER INFORMATION: ABCA1 M F4

<400> SEQUENCE: 28
gggttcgtcg gtttaagacg              20

<210> SEQ ID NO 29
<211> LENGTH: 29
<212> TYPE: DNA
<213> ORGANISM: Artificial Sequence
<220> FEATURE:
<223> OTHER INFORMATION: ABCA1 M R4

<400> SEQUENCE: 29
aaattccact aataccctta actaccgaa    29

<210> SEQ ID NO 30
<211> LENGTH: 20
<212> TYPE: DNA
<213> ORGANISM: Artificial Sequence
<220> FEATURE:
<223> OTHER INFORMATION: ABCA1 U F4

<400> SEQUENCE: 30
gggtttgttg gtttaagatg              20

<210> SEQ ID NO 31
<211> LENGTH: 30
<212> TYPE: DNA
<213> ORGANISM: Artificial Sequence
<220> FEATURE:
<223> OTHER INFORMATION: ABCA1 U R4

```
<400> SEQUENCE: 31
aacaaattcc actaataccc ttaactacca                                            30

<210> SEQ ID NO 32
<211> LENGTH: 21
<212> TYPE: DNA
<213> ORGANISM: Artificial Sequence
<220> FEATURE:
<223> OTHER INFORMATION: ABCA1 qRT F

<400> SEQUENCE: 32
ggactctggc ccaggagctg t                                                    21

<210> SEQ ID NO 33
<211> LENGTH: 20
<212> TYPE: DNA
<213> ORGANISM: Artificial Sequence
<220> FEATURE:
<223> OTHER INFORMATION: ABCA1 qRT R

<400> SEQUENCE: 33
ctcgggatgc ccgcagacaa                                                      20

<210> SEQ ID NO 34
<211> LENGTH: 22
<212> TYPE: DNA
<213> ORGANISM: Artificial Sequence
<220> FEATURE:
<223> OTHER INFORMATION: GAPDH qRT F

<400> SEQUENCE: 34
gaaggtcgga gtcaacggat tt                                                   22

<210> SEQ ID NO 35
<211> LENGTH: 21
<212> TYPE: DNA
<213> ORGANISM: Artificial Sequence
<220> FEATURE:
<223> OTHER INFORMATION: GAPDH qRT R

<400> SEQUENCE: 35
atgggtggaa tcatattgga a                                                    21
```

ABCA1 DOWNREGULATION IN PROSTATE CANCER

CROSS-REFERENCE TO RELATED APPLICATIONS

This application claims priority to U.S. Provisional Patent Application No. 61/749,507, filed Jan. 7, 2013, which is incorporated herein by reference in its entirety.

GOVERNMENT FUNDING

The present invention was made, in part, with government support under National Institute of Health Grant No. CA 154356 and HL098055. The U.S. Government has certain rights in this invention.

SEQUENCE LISTING

The instant application contains a Sequence Listing which has been submitted in ASCII format via EFS-Web and is hereby incorporated by reference in its entirety. Said ASCII copy, created on Jan. 1, 2014, is named CCF-021944USOR-D.txt and is 6,772 bytes in size.

BACKGROUND

Despite detection of prostate cancer at earlier stages and advances in the treatment of local as well as metastatic disease, there will still be an estimated 28,170 deaths due to prostate cancer in 2012. Men who die of prostate cancer have cancers with aggressive pathologic features that increase the risk of tumor progression and metastasis, even if they undergo radical therapy with curative intent. As such, the investigation of novel strategies to prevent the development of aggressive or advanced prostate cancer will be critical to lowering the morbidity and mortality attributed to this disease.

Epidemiologic studies have described a positive correlation between high serum cholesterol level and prostate cancer aggressiveness (Platz et al. Cancer Epidemiol Biomarkers Prev. 18(11):2807-13 (2009)) as well as a protective effect of statin use in lowering the risk of advanced prostate cancer. Mondul et al., Cancer Causes Control. 21(5):671-8 (2010). These reports, along with the discovery of de novo androgen synthesis in castration resistant prostate cancer (CRPC), have fueled a renewed interest in intratumoral cholesterol homeostasis due to the central role of cholesterol in steroidogenesis. Furthermore, excess intracellular cholesterol is incorporated into membrane lipid rafts, thereby stabilizing the raft structure and enhancing AKT signaling in prostate cancer cells. Oh et al., Prostate. 67(10):1061-9 (2007). Therefore, examining how prostate cancer cells manipulate intracellular cholesterol content is important for understanding prostate cancer biology.

Perturbation in cholesterol homeostasis is a well-known characteristic of cancer that was described more than fifty years ago. Siperstein M D, Fagan V M., Cancer Res. 24:1108-15 (1964). Subsequently, anecdotal reports described a beneficial effect of cholesterol lowering agents in the management of prostate cancer. Addleman W., N Engl J. Med., 287(20):1047 (1972). The introduction and widespread use of statins as cholesterol lowering agents in the prevention of heart disease allowed the collection of epidemiological data correlating prostate cancer risk and statin use. Although meta-analyses showed that statins had no effect on the overall risk of prostate cancer (Browning D R, Martin R M., Int J. Cancer. 120(4):833-43 (2007), other studies have shown that statin use is associated with a decreased risk of aggressive or advanced prostate cancer. Murtola et al., Cancer Epidemiol Biomarkers Prev. 16(11): 2226-32 (2007); Jacobs et al., Cancer Epidemiol Biomarkers Prev. 16(11):2213-7 (2007). Importantly, these cancers are potentially life threatening even after radical treatment. Thus, focusing on preventing the development or progression of aggressive prostate cancer is of utmost importance, and cholesterol may provide an opportune target. Indeed, recent reports suggest that statin use protects against prostate cancer with adverse pathologic characteristics (Mondul et al., J. Urol. 185(4):1268-73 (2011)) and improves progression free survival in men undergoing radiation therapy. Kollmeier et al., Int J Radiat Oncol Biol Phys. 79(3):713-8 (2011).

SUMMARY

Recent epidemiologic data show that low serum cholesterol level as well as statin use is associated with a decreased risk of developing aggressive or advanced prostate cancer, suggesting a role for cholesterol in aggressive prostate cancer development. Intracellular cholesterol promotes prostate cancer progression as a substrate for de novo androgen synthesis and through regulation of AKT signaling. By performing next-generation sequencing-based DNA methylome analysis, the inventors have discovered marked hypermethylation at the promoter of the major cellular cholesterol efflux transporter, ABCA1, in LNCaP prostate cancer cells. ABCA1 promoter hypermethylation renders the promoter unresponsive to trans-activation and leads to elevated cholesterol levels in LNCaP. ABCA1 promoter hypermethylation is enriched in intermediate to high grade prostate cancers and not detectable in benign prostate. Remarkably, ABCA1 down-regulation is evident in all prostate cancers examined, and expression levels are inversely correlated with Gleason grade. A decrease of ABCA1 expression in prostate tissue has also been shown to be associated with an increase in prostate cancer severity. The results suggest cancer-specific ABCA1 hypermethylation and loss of protein expression direct high intracellular cholesterol levels and hence contribute to an environment conducive to tumor progression.

Accordingly, in one aspect, the present invention provides a method of providing a prostate cancer prognosis in a subject having prostate cancer that includes obtaining a urine or prostate sample from the subject; determining the level of expression of ABCA1 in the sample; and comparing the level of expression of ABCA1 in the sample to the level of a control sample, wherein a decreased level of ABCA1 expression compared to the control indicates the subject has a more severe form of prostate cancer. In some embodiments, the level of expression of ABCA1 is determined by measuring the level of ABCA1 mRNA. In other embodiments, the level of expression of ABCA1 is determined by measuring the level of ABCA1 protein. ABCA1 protein levels can be determined by immunoassays using either polyclonal or monoclonal antibodies. In additional embodiments, the level of expression of ABCA1 is measured by detecting the methylation of an ABCA1 promoter region, wherein hypermethylation of the ABCA1 promoter region indicates a decreased level of ABCA1 expression.

In another aspect, the present invention provides a method of diagnosing prostate cancer in a subject that includes obtaining a urine or prostate sample from the subject; determining the level of expression of ABCA1 in the sample; and comparing the level of expression of ABCA1 in the sample to the level of a control sample, wherein a decreased level of ABCA1 expression compared to the control indicates the subject has prostate cancer. In some embodiments, the level of expression of ABCA1 is determined by measuring the level of ABCA1 mRNA. In other embodiments, the level of expression of ABCA1 is determined by measuring the level of ABCA1 protein. ABCA1 protein levels can be determined by immunoassays using either polyclonal or monoclonal antibodies. In additional embodiments, the level of expression of ABCA1 is measured by detecting the methylation of an ABCA1 promoter region, wherein hypermethylation of the ABCA1 promoter region indicates a decreased level of ABCA1 expression. In further embodiments, the method also includes the step of administering or prescribing a prostate cancer antitumor therapy to a subject having a decreased level of ABCA1 expression.

Another aspect of the present invention provides a kit for conducting diagnosis or prognosis of prostate cancer in a subject. The kit includes antibody specific for the ABCA1 protein, a reference value or control sample for ABCA1 levels, reagents necessary for conducting an immunoassay, and a package for holding the antibody, the reference value or control sample, and the reagents. In some embodiments, the kit includes instructions for using the kit to carry out a method of diagnosing or providing a prognosis of prostate cancer for a subject using the antibody, reagents, and the reference values or control samples. In further embodiments, the antibody used in the kit is a monoclonal antibody. In yet further embodiments, the antibody used in the kit was generated using the ABCA1 antigen sequence CRLFSDAR-RLLLYSQKDTSMKDM (SEQ ID NO: 1).

BRIEF DESCRIPTION OF THE FIGURES

The accompanying drawings, which are incorporated in and constitute a part of this specification, illustrate some embodiments disclosed herein, and together with the description, serve to explain principles of the exemplary embodiments disclosed herein.

DETAILED DESCRIPTION

Figure 1:
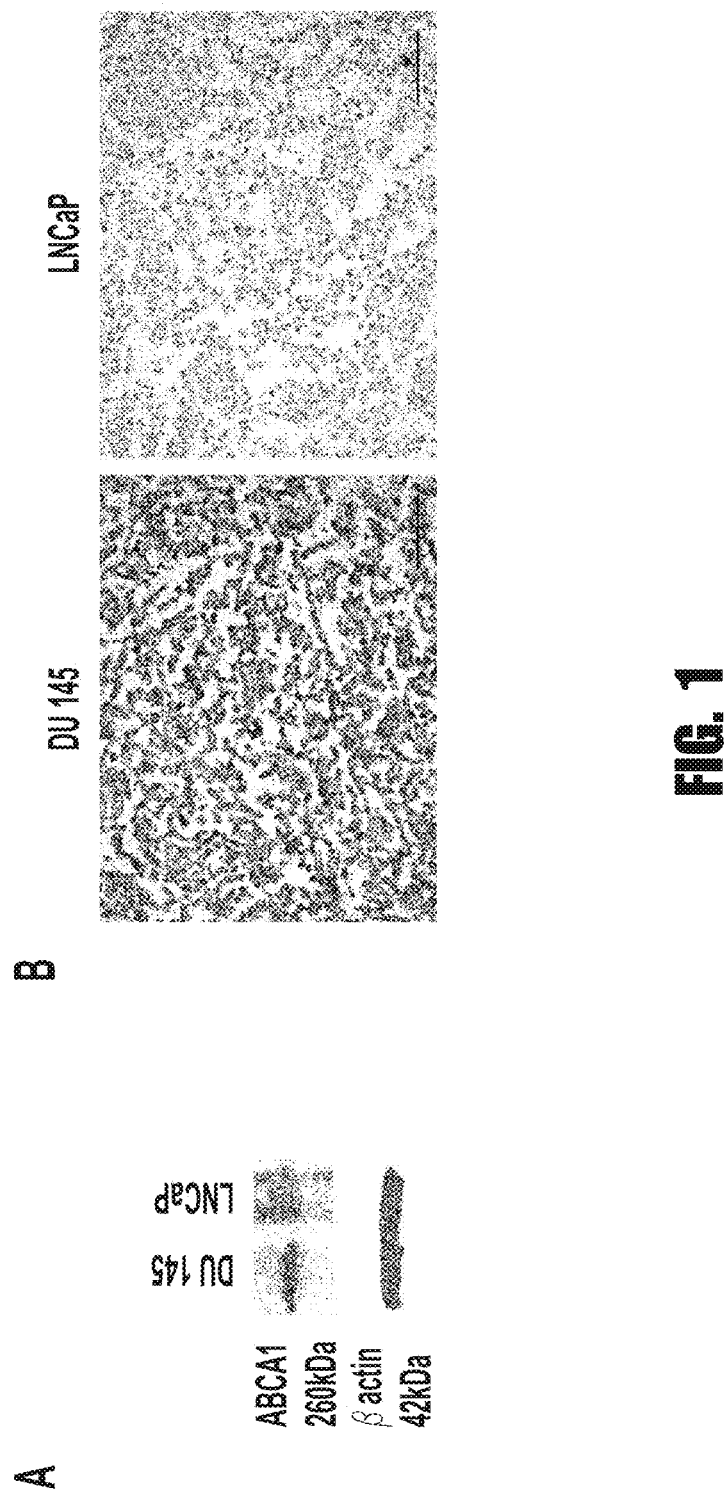
FIG. 1 provides images showing the validation of custom rabbit anti-ABCA1 antibody. (A) Western blotting of DU 145 and LNCaP cells using the custom rabbit anti-ABCA1 antibody and commercial mouse anti-ACTB (β-actin) as loading control. (B) Immunohistochemistry of DU 145 and LNCaP cell blocks using the custom rabbit anti-ABCA1 antibody. Cells were formalin fixed and paraffin embedded for sectioning and staining. The scale bar represents 0.1 mm.

The exemplary embodiments disclosed herein will now be described by reference to some more detailed exemplary embodiments, with occasional reference to the accompanying figures. These exemplary embodiments may, however, be embodied in different forms and should not be construed as limited to the embodiments set forth herein. Rather, these exemplary embodiments are provided so that this disclosure will be thorough and complete, and will fully convey the scope of the exemplary embodiments to those skilled in the art.

Unless otherwise defined, all technical and scientific terms used herein have the same meaning as commonly understood by one of ordinary skill in the art to which these exemplary embodiments belong. The terminology used in the description herein is for describing particular exemplary embodiments only and is not intended to be limiting of the exemplary embodiments. As used in the specification and the appended claims, the singular forms "a," "an," and "the" are intended to include the plural forms as well, unless the context clearly indicates otherwise. All publications, patent applications, patents, and other references mentioned herein are incorporated by reference in their entirety.

Unless otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present embodiments. At the very least, and not as an attempt to limit the application of the doctrine of equivalents to the scope of the claims, each numerical parameter should be construed in light of the number of significant digits and ordinary rounding approaches.

As used herein, the term "diagnosis" can encompass determining the presence and nature of disease or condition in a subject. "Diagnosis" can also encompass diagnosis in the context of rational therapy, in which the diagnosis guides therapy, including initial selection of therapy, modification of therapy (e.g., adjustment of dose and/or dosage regimen), and the like. Diagnosis does not imply certainty with regard to the nature of the disease or condition identified, but rather the substantial likelihood that the disease or condition is present. For example, a subject diagnosed as having prostate cancer may be 10× or 100× more likely to have prostate cancer relative to a subject that has not been diagnosed as having prostate cancer.

As used herein, the term "prognosis" refers to a prediction of the probable course and outcome of a disease, or the likelihood of recovery from a disease. Prognosis is distinguished from diagnosis in that it is generally already known that the subject has the disease, although prognosis and diagnosis can be carried out simultaneously. In the case of a prognosis for prostate cancer, the prognosis categorizes the relative severity of the prostate cancer, in a manner similar to that provided using Gleason scores.

The terms "individual," "host," "subject," and "patient" are used interchangeably herein, refers to a species of mammal, including, but not limited to, primates, including simians and humans, equines (e.g., horses), canines (e.g., dogs), felines, various domesticated livestock (e.g., ungulates, such as swine, pigs, goats, sheep, and the like), as well as domesticated pets and animals maintained in zoos.

As used herein, the term "therapeutically effective amount" is meant an amount of a compound effective to yield the desired therapeutic response. For example, an amount effective to delay the growth of or to cause a tumor to shrink, or prevent metastasis. The therapeutically effective amount will vary with such factors as the particular condition being treated, the physical condition of the patient, the type of mammal or animal being treated, the duration of the treatment, the nature of concurrent therapy (if any), and the specific formulations employed and the structure of the compounds or its derivatives.

The term antibody, as used herein, refers to single chain, two-chain, and multi-chain proteins and glycoproteins belonging to the classes of polyclonal, monoclonal, chimeric and hetero immunoglobulins (monoclonal antibodies being preferred); it also includes synthetic and genetically engineered variants of these immunoglobulins. "Antibody fragment" includes Fab, Fab', F(ab')$_2$, and Fv fragments, as well as any portion of an antibody having specificity toward a desired target epitope or epitopes.

The term monoclonal antibody, as used herein, refers to antibodies that are identical because they are produced by one type of immune cell that are all clones of a single parent cell. The monoclonal antibodies of the present invention can include intact monoclonal antibodies, antibody fragments, conjugates, or fusion proteins, which contain a $V_H$-$V_L$ pair where the complementarity determining region forms the antigen binding site.

The term chimeric antibody, as used herein, refers to an antibody which includes sequences derived from two different antibodies, which typically are of different species. Most typically, chimeric antibodies include human and non-human antibody fragments, generally human constant and non-human variable regions.

The term humanized antibody, as used herein, refers to an antibody derived from a non-human antibody, and a human antibody which retains or substantially retains the antigen-binding properties of the parent antibody but which is less immunogenic in humans.

The term antigen, as used herein, refers to a molecule or a portion of a molecule capable of being bound by an antibody which is additionally capable of inducing an animal to produce an antibody capable of binding to an epitope of that antigen. An antigen can have one or more than one epitope. The specific reaction referred to above is meant to indicate that the antigen will react, in a highly selective manner, with its corresponding antibody and not with the multitude of other antibodies which can be evoked by other antigens.

The term epitope, as used herein, refers to that portion of any molecule capable of being recognized by, and bound by, an antibody. In general, epitopes consist of chemically active surface groupings of molecules, for example, amino acids or sugar side chains, and have specific three-dimensional structural characteristics as well as specific charge characteristics. The epitopes of interest for the present invention are epitopes comprising amino acids.

In one aspect, the invention provides a method of providing a prostate cancer prognosis in a subject having prostate cancer that includes the steps of: (a) obtaining a urine or prostate sample from the subject; (b) determining the level of expression of ABCA1 in the sample; (c) comparing the level of expression of ABCA1 in the sample to the level of a control sample, wherein a decreased level of ABCA1 expression compared to the control indicates the subject has a more severe form of prostate cancer.

In another aspect, the invention provides a method of diagnosing prostate cancer in a subject that includes the steps of: (a) obtaining a urine or prostate sample from the subject; (b) determining the level of expression of ABCA1 in the sample; (c) comparing the level of expression of ABCA1 in the sample to the level of a control sample, wherein a decreased level of ABCA1 expression compared to the control indicates the subject has prostate cancer.

Urine and Prostate Samples

The expression of ABCA1 can be determined in any suitable biological sample. Preferably the biological sample is one associated with the prostate gland, such as a biopsy or fluid or cells associated with the prostate gland. Examples of suitable biological samples include tissue samples (e.g., a portion of an organ), a cell sample (e.g., peripheral leukocytes) and biological fluids such as urine and blood-related samples (e.g., whole blood, serum, plasma, and other blood-derived samples), urine, cerebral spinal fluid, bronchoalveolar lavage, and the like. In some embodiments, the biological sample is a prostate sample or a urine sample. Urine samples can include prostate epithelial cells which can be used for determining prostate-associated ABCA1 expression levels. Preferably, the prostate epithelial cells are collected in urine subsequent to conducting a digital rectal exam. Methods of obtaining samples and/or extracting nucleic acid or protein from such samples are described herein and known to those skilled in the art.

A biological sample may be fresh or stored (e.g. blood or blood fraction stored in a blood bank). Samples can be stored for varying amounts of time, such as being stored for an hour, a day, a week, a month, or more than a month. The biological sample (e.g., a urine or prostate tissue sample) may be a biological fluid expressly obtained for the assays of this invention or a biological fluid obtained for another purpose which can be subsampled for the assays of this invention.

In embodiments of the invention where promoter hypermethylation is evaluated, it is significant that the biological sample includes DNA that includes the ABCA1 promoter region. The biological sample including DNA can include any of the biological samples described herein. DNA (deoxyribonucleic acid), as is understood by those skilled in the art, is a molecule consisting of two long polymers of simple units called nucleotides with a backbone made of alternating sugars (deoxyribose) and phosphate groups that forms a double-stranded helix. The nucleotides include guanine, adenine, thymine, and cytosine, which are referenced using the letters G, A, T, and C. The term "nucleotide sequence," as used herein, refers to an oligonucleotide, nucleotide, or polynucleotide of single-stranded or double stranded DNA, or fragments thereof.

Determination of ABCA1 Expression

As used herein, the terms "expression of ABCA1" refers to the amount of ABCA1 protein that is present, the amount of mRNA transcribed from the ABCA1 gene that is present, or the level of methylation of the ABCA1 promoter, which affects the expression of the ABCA1 gene. The expression level can be detected with or without comparison to a level from a control sample or a level expected of a control sample. The expression level can be determined by measuring the amount of mRNA, or by measuring the amount of protein formed from the mRNA. The expression level of the ABCA1 gene may be decreased by at least about 2 fold, at least about 5 fold, at least about 10 fold, at least about 20 fold, or at least about 50 fold.

A variety of methods may be used to determine the level of expression of ABCA1 expression. Examples of suitable methods include immunoassay of ABCA1 levels or PCR analysis of ABCA1 mRNA. In some embodiments, the level of expression of the ABCA1 gene can be obtained by determining the relative levels of mRNA being expressed, using, for example, quantitative real-time polymerase chain reaction (qPCR). A key feature of qPCR is that the amplified DNA is detected as the reaction progresses in real time. This differs from standard PCR, where the product of the reaction is detected at its end. Two common methods for detection of products in real-time PCR are non-specific fluorescent dyes that intercalate with any double-stranded DNA, and sequence-specific DNA probes consisting of oligonucleotides that are labeled with a fluorescent reporter which permits detection only after hybridization of the probe with its complementary DNA target. See VanGuilder et al., Biotechniques 44 (5): 619-626 (2008).

Immunoassays

The level of ABCA1 protein is determined by an immunoassay. Antibodies specifically reactive with ABCA1, or derivatives thereof such as enzyme conjugates or labeled derivatives, may be used to detect ABCA1 in various biological samples, for example they may be used in any known immunoassays which rely on the binding interaction between an antigenic determinant of a protein and the antibodies. Examples of such assays are radioimmunoassays, enzyme immunoassay (e.g., ELISA), immunofluorescence, immunoprecipitation, latex agglutination, hemagglutination, and histochemical tests.

In some embodiments, and ELISA immunoassay is used. The term "ELISA" includes an enzyme-linked immunosorbent assay that employs an antibody or antigen bound to a solid phase and an enzyme-antigen or enzyme-antibody conjugate to detect and quantify the amount of an antigen (e.g., ABCA1) or antibody present in a sample. A description of the ELISA technique is found in Chapter 22 of the 4th Edition of Basic and Clinical Immunology by D. P. Sites et al., 1982, published by Lange Medical Publications of Los Altos, Calif. and in U.S. Pat. Nos. 3,654,090; 3,850,752; and 4,016,043, the disclosures of which are herein incorporated by reference. ELISA is an assay that can be used to quantitate the amount of ABCA1 in a sample. In particular, ELISA can be carried out by attaching on a solid support (e.g., polyvinylchloride) an antibody specific for an antigen or protein of interest. Cell extract or other sample of interest such as urine or blood can be added for formation of an antibody-antigen complex, and the extra, unbound sample is washed away. An enzyme-linked antibody, specific for a different site on the antigen is added. The support is washed to remove the unbound enzyme-linked second antibody. The enzyme-linked antibody can include, but is not limited to, alkaline phosphatase. The enzyme on the second antibody can convert an added colorless substrate into a colored product or can convert a non-fluorescent substrate into a fluorescent product. The ELISA-based assay method provided herein can be conducted in a single chamber or on an array of chambers and can be adapted for automated processes.

The present invention provides antibodies and antibody fragments specific for ABCA1 antigens. Antibodies are designed for specific binding, as a result of the affinity of complementary determining region of the antibody for the epitope of the target molecule (e.g., ABCA1). For example, an antibody specific for ABCA1 can be an antibody or antibody fragment capable of binding to an ABCA1 protein with a specific affinity of between $10^{-8}$ M and $10^{-11}$ M. In some embodiments, an antibody or antibody fragment binds to ABCA1 with a specific affinity of greater than $10^{-7}$M, $10^{-8}$M, $10^{-9}$M, $10^{-10}$M, or $10^{-11}$M, between $10^{-8}$M-$10^{-11}$ M, $10^{-9}$M-$10^{-10}$M, and $10^{-10}$M-$10^{-11}$M. In a preferred aspect, specific activity is measured using a competitive binding assay as set forth in Ausubel F M, (1994). Current Protocols in Molecular Biology. Chichester: John Wiley and Sons ("Ausubel"), which is incorporated herein by reference.

ABCA1 expression levels can also be determined using an immunoassay that includes the step of contacting the sample with an antibody that is specific for the ABCA1 protein. Antibodies specific for ABCA1 that are used in the methods of the invention may be obtained from scientific or commercial sources. Alternatively, isolated native ABCA1 or recombinant ABCA1 may be utilized to prepare antibodies, monoclonal or polyclonal antibodies, and immunologically active fragments (e.g., a Fab or (Fab)$_2$ fragment), an antibody heavy chain, an antibody light chain, humanized antibodies, a genetically engineered single chain $F_v$ molecule (Ladne et al., U.S. Pat. No. 4,946,778), or a chimeric antibody, for example, an antibody which contains the binding specificity of a murine antibody, but in which the remaining portions are of human origin. Antibodies including monoclonal and polyclonal antibodies, fragments and chimeras, may be prepared using methods known to those skilled in the art. Preferably, antibodies used in the methods of the invention are reactive against ABCA1 if they bind with a $K_a$ of greater than or equal to $10^7$ M. In some embodiments of the invention, the immunoassay includes the step of contacting the sample with a polyclonal antibody that is specific for the ABCA1 protein. Preferably, polyclonal antibodies from the mouse, rabbit, chicken, or llama are utilized.

In other embodiments of the invention, the immunoassay includes the step of contacting the sample with a monoclonal antibody that is specific for the ABCA1 protein. To produce monoclonal antibodies, a host mammal is inoculated with an ABCA1 protein or peptide and then boosted. Spleens are collected from inoculated mammals a few days after the final boost. Cell suspensions from the spleens are fused with a tumor cell in accordance with the general method described by Kohler and Milstein (Nature, 1975, 256:495-497). In order to be useful, a peptide fragment must contain sufficient amino acid residues to define the epitope of the ABCA1 molecule being detected.

If the fragment is too short to be immunogenic, it may be conjugated to a carrier molecule. Some suitable carrier molecules include keyhole limpet hemocyanin and bovine serum albumin. Conjugation may be carried out by methods known in the art. One such method is to combine a cysteine residue of the fragment with a cysteine residue on the carrier molecule. The peptide fragments may be synthesized by methods known in the art. Some suitable methods are described by Stuart and Young in "Solid Phase Peptide Synthesis," Second Edition, Pierce Chemical Company (1984).

Purification of the antibodies or fragments can be accomplished by a variety of methods known to those of skill including, precipitation by ammonium sulfate or sodium sulfate followed by dialysis against saline, ion exchange chromatography, affinity or immunoaffinity chromatography as well as gel filtration, zone electrophoresis, etc. (Goding in, Monoclonal Antibodies: Principles and Practice, 2d ed., pp. 104-126, Orlando, Fla., Academic Press). It is preferable to use purified antibodies or purified fragments of the antibodies having at least a portion of a ABCA1 binding region, including such as Fv, F(ab')$_2$, Fab fragments (Harlow and Lane, 1988, Antibody, Cold Spring Harbor Laboratory Press) for the detection of ABCA1 in a biological sample obtained from a subject.

For use in detection and/or prognosis of prostate cancer, the purified antibodies can be covalently attached, either directly or via linker, to a compound which serves as a reporter group to permit detection of the presence of ABCA1. A variety of different types of substances can serve as the reporter group, including but not limited to enzymes, dyes, radioactive metal and non-metal isotopes, fluorogenic compounds, fluorescent compounds, etc. Methods for preparation of antibody conjugates of the antibodies (or fragments thereof) of the invention useful for detection and monitoring are described in U.S. Pat. Nos. 4,671,958; 4,741,900 and 4,867,973.

In some embodiments of the invention, preferred binding epitopes may be identified from a known ABCA1 gene sequence and its encoded amino acid sequence and used to generate ABCA1 antibodies with high binding affinity. Also, identification of binding epitopes on ABCA1 can be used in the design and construction of preferred antibodies. For example, a DNA encoding a preferred epitope on ABCA1 may be recombinantly expressed and used to select an antibody which binds selectively to that epitope. Accordingly, in one embodiment, the immunoassay includes the step of contacting the sample with an antibody that was generated using the ABCA1 antigen sequence CRLFSDAR-RLLLYSQKDTSMKDM (SEQ ID NO: 1). The selected antibodies then are exposed to the sample under conditions sufficient to allow specific binding of the antibody to the specific binding epitope on ABCA1 and the amount of complex formed then detected. Specific antibody methodologies are well understood and described in the literature. A more detailed description of their preparation can be found, for example, in Practical Immunology, Butt, W. R., ed., Marcel Dekker, New York, 1984.

In some embodiments, the level of expression of ABCA1 is determined by measuring the level of ABCA1 protein. While use of an immunoassay is preferred, the level of ABCA1 expression can also be determined by purify the expressed ABCA1 protein and directly determining its level of expression. Protein purification techniques are well known to those of skill in the art. These techniques involve, at one level, the crude fractionation of the cellular milieu to polypeptide and non-polypeptide fractions. Having separated the polypeptide from other proteins, the polypeptide of interest may be further purified and/or quantified using chromatographic and electrophoretic techniques to achieve partial or complete purification (or purification to homogeneity). Analytical methods particularly suited to the preparation of a pure peptide are immunohistochemistry, ion-exchange chromatography, exclusion chromatography; polyacrylamide gel electrophoresis; isoelectric focusing. A particularly efficient method of purifying peptides is fast protein liquid chromatography or even HPLC.

ABCA1 Promoter Hypermethylation

Another embodiment of the method of providing a diagnosis or prognosis of prostate cancer involves determining the level of ABCA1 gene expression by detecting the level of methylation of the ABCA1 promoter region. Hypermethylation of the ABCA1 promoter region corresponds to a decreased level of ABCA1 gene expression. As used herein, the term "hypermethylation" refers to the methylation state corresponding to an increased presence of 5-methyl-cytosine ("5-mCyt") at one or a plurality of CpG dinucleotides within a DNA sequence of a test DNA sample, relative to the amount of 5-mCyt found at corresponding CpG dinucleotides within a normal control DNA sample. In particular, hypermethylation refers to the methylation of a CpG island. As described herein, methylation of the ABCA1 promoter results in decreased formation of the ABCA1 promoter, resulting in a lower level of ABCA1 expression.

The method of diagnosing or providing a prognosis for prostate cancer includes the steps of: (a) obtaining a biological sample including DNA from a subject; (b) determining the level of methylation of the ABCA1 promoter region in the biological sample; and (c) comparing the level of methylation of the ABCA1 promoter region in the biological sample to a control value for ABCA1 promoter expression. A higher level of methylation of the ABCA1 promoter region in the biological sample relative to methylation of the ABCA1 promoter region control value provides a diagnosis that the subject has, or has a substantially increased risk of having, prostate cancer, or a prognosis of a more severe form of prostate cancer. Nucleic acids contained in a sample used for detection of methylated CpG islands may be extracted by a variety of techniques such as that described by Sambrook, et al. (Molecular Cloning: A Laboratory Manual, Cold Spring Harbor, N.Y., 1989).

DNA methylation is essential for normal development and is associated with a number of key processes including genomic imprinting, X-chromosome inactivation, suppression of repetitive elements, and carcinogenesis. Between 60% and 90% of all CpGs are methylated in mammals. Unmethylated CpGs are often grouped in clusters called CpG islands, which are present in the 5' regulatory regions of many genes. As used herein, the term "methylation" refers to the covalent attachment of a methyl group at the C5-position of the nucleotide base cytosine within the CpG dinucleotides of gene regulatory region. The term "methylation state" or "methylation status" or "methylation level" or "the degree of methylation" refers to the presence or absence of 5-mCyt at one or a plurality of CpG dinucleotides within a DNA sequence.

A wide variety of methods are available for determining gene methylation, such as methylation of the ABCA1 promoter region. A number of these methods are described herein.

Detection of Differential Methylation-Methylation-Specific PCR

When genomic DNA is treated with bisulfite, cytosine in the 5'-CpG'-3 region remains intact, if it was methylated, but the cytosine changes to uracil, if it was unmethylated. Accordingly, the method of diagnosis can include the step of detecting methylation of the ABCA1 promoter region includes the step of bringing the ABCA1 promoter region into contact with sodium bisulfite under conditions suitable to modify unmethylated cytosine of the ABCA1 promoter region into uracil. Based on the base sequence converted after bisulfite treatment, PCR primer sets corresponding to a region having the 5'-CpG-3' base sequence are constructed. Herein, the constructed primer sets are two kinds of primer sets: a primer set corresponding to the methylated base sequence, and a primer set corresponding to the unmethylated base sequence. When genomic DNA is converted with bisulfite and then amplified by PCR using the above two kinds of primer sets, the PCR product is detected in the PCR mixture employing the primers corresponding to the methylated base sequence, if the genomic DNA was methylated, but the genomic DNA is detected in the PCR mixture employing the primers corresponding to the unmethylated, if the genomic DNA was unmethylated. This methylation can be quantitatively analyzed by agarose gel electrophoresis.

Detection of Differential Methylation—Real-Time Methylation Specific PCR

Real-time methylation-specific PCR is a real-time measurement method modified from the methylation-specific PCR method and includes treating genomic DNA with bisulfite, designing PCR primers corresponding to the methylated base sequence, and performing real-time PCR using the primers. Methods of detecting the methylation of the genomic DNA include two methods: a method of detection using a TaqMan probe complementary to the amplified base sequence; and a method of detection using SYBR green (an asymmetrical cyanine dye used as a nucleic acid stain). Real-time methylation-specific PCR allows selective quantitative analysis of methylated DNA. A standard curve is plotted using an in vitro methylated DNA sample, and a gene containing no 5'-CpG-3' sequence in the base sequence is also amplified as a negative control group for standardization to quantitatively analyze the degree of methylation.

Detection of Differential Methylation—Bisulfite Sequencing Method

Another method for detecting a methylated CpG-containing nucleic acid comprises the steps of: bringing a nucleic acid-containing sample into contact with an agent that modifies unmethylated cytosine; and amplifying the CpG-containing nucleic acid in the sample using CpG-specific oligonucleotide primers, wherein the oligonucleotide primers distinguish between modified methylated nucleic acid and non-methylated nucleic acid and detect the methylated nucleic acid. The amplification step is optional and desirable, but not essential. The method relies on the PCR reaction to distinguish between modified (e.g., chemically modified) methylated DNA and unmethylated DNA. Such methods are described in U.S. Pat. No. 5,786,146 relating to bisulfite sequencing for detection of methylated nucleic acid. This method is also referred to herein as combined bisulfite restriction analysis.

Detection of Differential Methylation—Pyrosequencing

The pyrosequencing method is a quantitative real-time sequencing method modified from the bisulfite sequencing method. Similarly to bisulfite sequencing, genomic DNA is converted by bisulfite treatment, and then, PCR primers corresponding to a region containing no 5'-CpG-3' base sequence are constructed. Specifically, the genomic DNA is treated with bisulfite, amplified using the PCR primers, and then subjected to real-time base sequence analysis using a sequencing primer. The degree of methylation is expressed as a methylation index by analyzing the amounts of cytosine and thymine in the 5'-CpG-3' region.

Detection of Differential Methylation—PCR Using Methylated DNA-specific binding protein, quantitative PCR, And DNA Chip Assay When a protein binding specifically to methylated DNA is mixed with DNA, the protein binds specifically only to the methylated DNA. Thus, either PCR using a methylation-specific binding protein or a DNA chip assay allows selective isolation of only methylated DNA. Genomic DNA is mixed with a methylation-specific binding protein, and then only methylated DNA was selectively isolated. The isolated DNA is amplified using PCR primers corresponding to the promoter region, and then methylation of the DNA is measured by agarose gel electrophoresis.

In addition, methylation of DNA can also be measured by a quantitative PCR method, and methylated DNA isolated with a methylated DNA-specific binding protein can be labeled with a fluorescent probe and hybridized to a DNA chip containing complementary probes, thereby measuring methylation of the DNA. Herein, the methylated DNA-specific binding protein may be, but not limited to, McrBt.

Detection of Differential Methylation—Methylation-Sensitive Restriction Enzyme

Detection of differential methylation can be accomplished by bringing a nucleic acid sample into contact with a methylation-sensitive restriction endonuclease that cleaves only unmethylated CpG sites. In a separate reaction, the sample is further brought into contact with an isoschizomer of the methylation-sensitive restriction enzyme that cleaves both methylated and unmethylated CpG-sites, thereby cleaving the methylated nucleic acid. Specific primers are added to the nucleic acid sample, and the nucleic acid is amplified by any conventional method. The presence of an amplified product in the sample treated with the methylation-sensitive restriction enzyme but absence of an amplified product in the sample treated with the isoschizomer of the methylation-sensitive restriction enzyme indicates that methylation has occurred at the nucleic acid region assayed. However, the absence of an amplified product in the sample treated with the methylation-sensitive restriction enzyme together with the absence of an amplified product in the sample treated with the isoschizomer of the methylation-sensitive restriction enzyme indicates that no methylation has occurred at the nucleic acid region assayed.

As used herein, the term "methylation-sensitive restriction enzyme" refers to a restriction enzyme (e.g., SmaI) that includes CG as part of its recognition site and has activity when the C is methylated as compared to when the C is not methylated. Non-limiting examples of methylation-sensitive restriction enzymes include MspI, HpaII, BssHII, BstUI and NotI. Such enzymes can be used alone or in combination. Examples of other methylation-sensitive restriction enzymes include, but are not limited to SacII and EagI. The isoschizomer of the methylation-sensitive restriction enzyme is a restriction enzyme that recognizes the same recognition site as the methylation-sensitive restriction enzyme but cleaves both methylated and unmethylated CGs. An example thereof includes MspI.

Primers for use in the methods for detecting DNA methylation are designed to be "substantially" complementary to each strand of the locus to be amplified and include the appropriate G or C nucleotides. This means that the primers must be sufficiently complementary to hybridize with their respective strands under polymerization reaction conditions. The primers are used in the amplification process, which is an enzymatic chain reaction (e.g., PCR) in which that a target locus exponentially increases through a number of reaction steps. Typically, one primer is homologous with the negative (−) strand of the locus (antisense primer), and the other primer is homologous with the positive (+) strand (sense primer). After the primers have been annealed to denatured nucleic acid, the nucleic acid chain is extended by an enzyme such as DNA Polymerase I (Klenow), and reactants such as nucleotides, and, as a result, + and − strands containing the target locus sequence are newly synthesized. When the newly synthesized target locus is used as a template and subjected to repeated cycles of denaturing, primer annealing, and extension, exponential synthesis of the target locus sequence occurs. The resulting reaction product is a discrete nucleic acid duplex with termini corresponding to the ends of specific primers employed. For example, in one embodiment of the invention, the PCR primers used selected from the group consisting of the primers shown in Table 1. In particular, these PCR primers are suitable for DNA methylation analysis using the combined bisulfite restriction analysis method.

The amplification reaction is the polymerase chain reaction (PCR) which is well known and commonly used in the art. However, alternative methods such as real-time PCR or linear amplification using isothermal enzyme may also be used. In addition, multiplex amplification reactions may also be used.

Controls

Control values are based upon the level of ABCA1 expression or methylation of the ABCA1 promoter region in comparable samples obtained from a reference cohort. In certain embodiments, the reference cohort is the general population. For example, the reference cohort can be a select population of human subjects. In certain embodiments, the reference cohort is comprised of individuals who have not previously had any signs or symptoms indicating the presence of prostate cancer.

The control value can take a variety of forms. The control value can be a single cut-off value, such as a median or mean. Control values for the level of ABCA1 expression or the methylation of the ABCA1 promoter region in biological samples obtained, such as for example, mean levels, median levels, or "cut-off" levels, are established by assaying a large sample of individuals in the general population or the select population and using a statistical model such as the predictive value method for selecting a positivity criterion or receiver operator characteristic curve that defines optimum specificity (highest true negative rate) and sensitivity (highest true positive rate) as described in Knapp, R. G., and Miller, M. C. (1992). Clinical Epidemiology and Biostatistics. William and Wilkins, Harual Publishing Co. Malvern, Pa., which is specifically incorporated herein by reference.

Prostate Cancer

Prostate cancer is cancer found in the prostate, which is an exocrine gland of the male reproductive system, and exists directly under the bladder, in front of the rectum. Most prostate cancers are adenocarcinomas. Prostate cancer, as used herein, includes precancer forms such as prostatic intraepithelial neoplasia. The severity of prostate cancer is generally evaluated using a Gleason score, with range from 2 to 10, obtained by adding the score for a predominant pattern to a secondary pattern, with pattern scores ranging from 1 to 5 and increasing score numbers indicating a more advanced and/or aggressive form of prostate cancer. For example, a Gleason score of 6 or more can indicate the presence of a worse than average, or severe, form of prostate cancer. In some embodiments of the invention, the subject has one or more symptoms of prostate cancer. Symptoms of prostate cancer include trouble urinating, decreased force in the stream of urine, blood in the urine, blood in the semen, general pain in the lower back, hips or thighs, discomfort in the pelvic area, bone pain, and erectile dysfunction. Additional screening and diagnostic tests can be performed to help determine if a subject has prostate cancer. Screening tests include a digital rectal exam, and a test for higher than normal levels of prostate-specific antigen, which diagnostic tests include a transrectal ultrasound or a biopsy of prostate tissue which is evaluated for the presence of prostate cancer cells.

Kits

In one aspect, the invention provides kits that include the elements for providing a diagnosis or prognosis of prostate cancer in a subject by determining the level of ABCA1 expression. The kit can be used for quantitatively detecting ABCA1 expression levels in a sample such as prostate tissue or urine. Kits can be configured to determine ABCA1 expression by determining ABCA1 protein levels, ABCA1 mRNA levels, or the degree of ABCA1 promoter hypermethylation. For example, kits configured to determine the level of ABCA1 protein levels can include antibodies specific for ABCA1. This embodiment provides a kit for conducting diagnosis or prognosis of prostate cancer in a subject that includes an antibody specific for the ABCA1 protein, a reference value or control sample for ABCA1 levels, reagents necessary for conducting an immunoassay, and a package for holding the antibody, the reference value or control sample, and the reagents. The components of the kits can be packaged either in aqueous medium or in lyophilized form. The kit can also include antibodies against the antibodies labeled with an enzyme; and a substrate for the enzyme, a solid support such as microtiter multi-well plates, standards, assay diluent, wash buffer, and adhesive plate covers.

Antibodies used in the kits can be provided in the form of conjugates in which a label is attached, such as a radioactive metal ion or a moiety, the components of such conjugates can be supplied either in fully conjugated form, in the form of intermediates or as separate moieties to be conjugated by the user of the kit. The antibodies included can be polyclonal antibodies, monoclonal antibodies, humanized antibodies, chimeric antibodies, or antibody fragments. In some embodiments, the antibody included was generated using the ABCA1 antigen sequence CRLFSDARRLLLY-SQKDTSMKDM (SEQ ID NO: 1).

In some embodiments, the kit includes instructions for using the kit to carry out a method of diagnosing or providing a prognosis of prostate cancer for a subject using the antibody, reagents, and the reference values or control samples. Instructions included in kits can be affixed to packaging material or can be included as a package insert. While the instructions are typically written or printed materials they are not limited to such. Any medium capable of storing such instructions and communicating them to an end user is contemplated by this disclosure. Such media include, but are not limited to, electronic storage media (e.g., magnetic discs, tapes, cartridges, chips), optical media (e.g., CD ROM), and the like. As used herein, the term "instructions" can include the address of an internet site that provides the instructions.

In other embodiments, a kit for diagnosing prostate cancer by evaluating ABCA1 promoter hypermethylation is provided. The kit includes a carrier compartmentalized to include a plurality of containers and to receive a DNA sample including the ABCA1 promoter region from a subject therein. The reagents included in the kit will vary depending on the particular technique being used to identify ABCA1 promoter hypermethylation. For example, in one embodiment, the kit includes a first container including sodium bisulfite, and the solvents and reagents necessary to selectively convert unmethylated cytosine of the DNA sample into uracil; a second container containing a PCR primer pair corresponding to the methylated base sequence of a ABCA1 promoter region and the solvents and reagents necessary to obtain an amplified base sequence; and a third container containing a labeled probe complementary to the amplified base sequence. The kit also includes means for detecting the labeled probe to quantitatively analyze the amount of methylation of the ABCA1 promoter region; and an ABCA1 promoter region control.

In other embodiments, kits designed to detect methylation of the ABCA1 promoter region using DNA methylation detection methods other than bisulfite sequencing methods can be used. Examples of other DNA methylation detection include any of the DNA methylation detection methods described herein, such as pyrosequencing and cleavage of unmethylated CpG sizes using a methylation-sensitive restriction enzyme. For all of these kits, if a higher level of methylation of the ABCA1 promoter region is found relative to that present in controls, or the ABCA1 promoter region is found to be hypermethylated, this indicates that a subject evaluated using the kit can be diagnosed as having prostate cancer.

Treatment of Prostate Cancer in Subjects Having ABCA1 Promoter Methylation and/or ABCA1 Underexpression Further embodiments include providing a therapeutic intervention for a subject identified as having a substantially increased risk of having prostate cancer. The therapeutic invention can be provided as a follow-up step to a diagnosis of a subject having prostate cancer as a result of carrying out any of the methods of diagnosis described herein. Examples of types of treatment for prostate cancer are surgery (e.g., radical prostatectomy, pelvic lymphadenectomy, transurethral resection of the prostate, orchiectomy, or cryosurgery), radiation therapy (e.g., internal radiation therapy using strontium-89, proton beam radiation therapy) hormone therapy, chemotherapy, biologic therapy, targeted therapy (e.g., monoclonal antibody therapy), and high-intensity focused ultrasound.

Several of the therapeutic interventions described above can be characterized as treatment with an anticancer agent. These include forms of hormone therapy, chemotherapy, and biologic therapy. Examples of anticancer agents useful for hormone therapy include luteinizing hormone-releasing hormone agonists, antiandrogens, ketoconazole, aminoglutethimide, and estrogens. Examples of chemotherapeutic and biologic agents include Cabazitaxel, Degarelix, Taxotere (Docetaxel), Enzalutamide, Jevtana (Cabazitaxel), Lupron or Viadur (Leuprolide Acetate), Prednisone, Prolia or Xgeva (Denosumab), Provenge (Sipuleucel-T), Xofigo (Radium 223 Dichloride), Sipuleucel-T, Xtandi (Enzalutamide), and Zytiga (Abiraterone Acetate).

The following example is included for purposes of illustration and is not intended to limit the scope of the invention.

EXAMPLE

Example 1: Dysregulation of Cholesterol Homeostasis in Human Prostate Cancer Through Loss of ABCA1

To understand the role that altered DNA methylation patterns play in prostate cancer development, MBD-isolated Genome Sequencing (MiGS) were used to construct genome-wide DNA methylation profiles in the common prostate cell line models, PrEC, LNCaP, and DU 145. Using unbiased global analysis, it was discovered that dense hypermethylation in the 5' regulatory regions of the cholesterol efflux transporter, ATP-binding cassette, sub family A, member 1 (ABCA1), in LNCaP cells but not in PrEC or DU 145 cells. Given data suggesting that loss of cellular cholesterol homeostasis is important in prostate cancer, the inventors proceeded to delineate the biological relevance of this epigenetic modification. The inventors report that DNA hypermethylation at ABCA1 promoter in LNCaP cells effectively suppresses basal expression and prevents full induction by a trans-activator. Loss of ABCA1 expression results in retention of intracellular cholesterol. Furthermore, ABCA1 hypermethylation is exclusively detected in intermediate and high grade prostate cancers, suggesting that epigenetic inactivation of ABCA1 is involved in prostate cancer progression. Finally, significant decrease and complete loss of ABCA1 protein expression are evident in all prostate cancers examined in our study. Together, these findings indicate that ABCA1 is an important regulator of intracellular cholesterol levels in prostate epithelial cells and that its pervasive inactivation in prostate cancers likely provides a milieu favorable for tumor progression by permitting the accumulation of intracellular cholesterol.

Materials and Methods
DNA Methylation Analysis

DNA methylome profiles for PrEC, LNCaP, and DU 145 were generated using MiGS as previously described. Serre et al., Nucleic Acids Res. 38(2):391-9 (2010). The sequencing reads generated and used in this manuscript are deposited in the NCBI Sequence Read Archive (SRA) under the accession number SRA049689.1. The raw sequencing reads for each sample were mapped to the reference human genome (UCSC Hg18) using Bowtie. Langmead et al., Genome Biol. 10(3):R25 (2009). Bisulfite sequencing and methylation-specific PCR (MSP) of the ABCA1 promoter was performed as previously described (Yan et al., PLoS ONE. 2011; 6(6):e20628 (2011). See Table 1 for a list of the primers used.

TABLE 1

Primer Information

| Primer name | Sequence | Size (bp) | Tm (° C.) |
|---|---|---|---|
| Bisulfite sequencing primers | | | |
| ABCA1 BSF1 | GGTTAGAATAGATTAGTTTTTTAAGAAT (SEQ ID NO: 2) | 310 | 57 |
| ABCA1 BSR1 | AACTCTAATAACCCCAAAACTCTAC (SEQ ID NO: 3) | | |
| ABCA1 BSF2 | ATTTAGGAGGTTGAGGTAGGAGAAT (SEQ ID NO: 4) | 408 | 60 |
| ABCA1 BSR2 | AAATACCAACACTAAATCTTCACTC (SEQ ID NO: 5) | | |
| ABCA1 BSF3 | GAGGGAGGATTGGGTATTTTATTT (SEQ ID NO: 6) | 181 | 60 |
| ABCA1 BSR3 | TTCAACTTATTAACCAAACTAATCTC (SEQ ID NO: 7) | | |
| ABCA1 BSF4 | GTAGAGTTTTGGGGTTATTAGAGTT (SEQ ID NO: 8) | 251 | 50 |
| ABCA1 BSR4 | AAAAACTTATCAAAAAATAAAAAAAA (SEQ ID NO: 9) | | |
| ABCA1 BSF5 | GGTTTTTGTTTATGTAGTTTAGTTATTTAG (SEQ ID NO: 10) | 156 | 60 |
| ABCA1 BSR5 | AACCCTAAAACACCTACTATACCCTC (SEQ ID NO: 11) | | |
| ABCA1 BSF6 | AGGGTATAGTAGGTGTTTTAGGGTT (SEQ ID NO: 12) | 169 | 60 |
| ABCA1 BSR6 | CAAAATTTAAAAAAAACAAATTCCACTA (SEQ ID NO: 13) | | |
| ABCA1 BSF8 | TTTTTTTATTTTTTGATAAGTTTTT (SEQ ID NO: 14) | 327 | 50 |
| ABCA1 BSR8 | CTAAATAACTAAACTACATAAACAAAAAC (SEQ ID NO: 15) | | |
| MSP primers | | | |
| ABCA1 M F1 | TATTAGAGTTCGTATTAGGATATCGT (SEQ ID NO: 16) | 159 | 50 |
| ABCA1 M R1 | CTTAAACGTTATTATTTTATTTCGAA (SEQ ID NO: 17) | | |
| ABCA1 U F1 | GGTTATTAGAGTTTGTATTAGGATATTGT (SEQ ID NO: 18) | 170 | 50 |
| ABCA1 U R1 | ATAACTTACTTAAACATTATTATTTTATTTCA (SEQ ID NO: 19) | | |
| ABCA1 M F2 | ATAAGGAGTAAAGCGTTTTGAGAATC (SEQ ID NO: 20) | 129 | 50 |
| ABCA1 M R2 | TACGAACGAAAATAAATAAAACCGAA (SEQ ID NO: 21) | | |
| ABCA1 U F2 | AAGGAGTAAAGTGTTTTGAGAATTGG (SEQ ID NO: 22) | 127 | 50 |
| ABCA1 U R2 | TACAAACAAAAATAAATAAAACCAAA (SEQ ID NO: 23) | | |
| ABCA1 M F3 | TAGAAAGTACGTGGAGTCGGG (SEQ ID NO: 24) | 148 | 58 |
| ABCA1 M R3 | AAAAAAAAAAACGCAAACCGCGAA (SEQ ID NO: 25) | | |

TABLE 1 -continued

Primer Information

| Primer name | Sequence | Size (bp) | Tm (° C.) |
|---|---|---|---|
| ABCA1 U F3 | TAGAAAGTATGTGGAGTTGGGG (SEQ ID NO: 26) | 140 | 58 |
| ABCA1 U R3 | ACACAAACCACAAACCCTAAAACA (SEQ ID NO: 27) | | |
| ABCA1 M F4 | GGGTTCGTCGGTTTAAGACG (SEQ ID NO: 28) | 100 | 58 |
| ABCA1 M R4 | AAATTCCACTAATACCCTTAACTACCGAA (SEQ ID NO: 29) | | |
| ABCA1 U F4 | GGGTTTGTTGGTTTAAGATG (SEQ ID NO: 30) | 103 | 58 |
| ABCA1 U R4 | AACAAATTCCACTAATACCCTTAACTACCA (SEQ ID NO: 31) | | | qRT-PCR primers

| ABCA1 qRT F | GGACTCTGGCCCAGGAGCTGT (SEQ ID NO: 32) | 143 | 60 |
|---|---|---|---|
| ABCA1 qRT R | CTCGGGATGCCCGCAGACAA (SEQ ID NO: 33) | | |
| GAPDH qRT F | GAAGGTCGGAGTCAACGGATTT (SEQ ID NO: 34) | 148 | 55 |
| GAPDH qRT R | ATGGGTGGAATCATATTGGAA (SEQ ID NO: 35) | | |

Cell Culture, Transfection, and Luciferase Assay

PrEC (Lonza, Walkersville, Md.) was cultured in PrEGM according to the manufacturer's instructions. LNCaP and DU 145 (ATCC, Manassas, Va.) were cultured in RPMI 1640 supplemented with 10% FBS. All three cell lines were obtained directly from the cell banks, and the identities of the cell lines were verified per the cell banks' protocols. Cells were treated with 10 μM T0901317 (Sigma, St. Louis, Mo.) for 24 hours or 5 μM 5-aza-2'-deoxycytidine (Sigma, St. Louis, Mo.) for 7 days, or a combination of the two compounds. ABCA1 promoter (−1132 to +112 relative to the transcription start site) was amplified by PCR and subcloned into the pGL4.20 (Promega, Madison, Wis.). Methylated ABCA1 promoter was in vitro DNA methylated using SssI (NEB, Ipswich, Mass.) and ligated into pGL4.20 prior to transfection. The reporter construct was co-transfected with pGL 4.74 vector into DU 145 cells using Nucleofection (Lonza, Walkersville, Md.). Reporter luciferase activity was measured and normalized to control Renilla luciferase activity for each sample. The mean±SEM from triplicate experiments for each experimental group was plotted for comparisons. The different groups were compared using one way ANOVA with Bonferroni's multiple comparison test.

Gene Expression and Western Blot

Expression of ABCA1 and GAPDH mRNA was measured by realtime RT-PCR as previously described (Yan et al.). The relative fold change in expression was calculated using the $2^{-\Delta\Delta CT}$ method by normalizing to GAPDH mRNA expression in each sample and compared to LNCaP mock treated cells. The mean±SEM from triplicate experiments for each experimental group was plotted, and comparisons between each sample group against LNCaP mock treated cells were performed using one way ANOVA with Bonferroni's multiple comparison test. For Western blot analysis of ABCA1 and β actin (ACTB), 15 μg cell lysate per sample were resolved in 4-12% Bis-Tris gel (Life Technologies, Grand Island, N.Y.), transferred onto nylon membranes, and probed with rabbit anti-ABCA1 (Novus Biologicals, Littleton, Colo.) and mouse anti-ACTB (Sigma, St. Louis, Mo.). For gene expression microarray analysis, total RNA was extracted with TRIzol (Life Technologies, Grand Island, N.Y.), followed by DNase I treatment. The RNA samples were labeled and hybridized according to the manufacture's protocol to the Illumina HumanRef-8 v3.0 expression beadchips (Illumina, San Diego, Calif.) in triplicates. The expression results generated and used in this manuscript are deposited with the Gene Expression Omnibus under the accession number GSE35401. Differential gene expression analysis was performed using the Illumina GenomeStudio v2009.1 (Illumina, San Diego, Calif.).

Cellular Cholesterol Analysis

For filipin staining, LNCaP and DU 145 cells were grown on glass coverslips, fixed in 3% paraformaldehyde, and stained with 50 μg/mL filipin (Sigma, St. Louis, Mo.). Images were acquired using QCapturePro software (QImaging, Surrey, Canada) at the designated magnifications and fixed aperture and exposure time for both cell lines. Biochemical quantification of intracellular cholesterol was performed as previously described. Robinet et al., J Lipid Res. 51(11):3364-9 (2010). The different groups were compared using one way ANOVA with Bonferroni correction. For analysis of cholesterol efflux, cells were labeled with 0.5 μCi/mL [$^3$H]-cholesterol in RPMI containing 1% FBS for 16 hours at 37° C. After labeling, cells were chased for 4 hours at 37° C. in RPMI with or without acceptors (10 μg/mL APOA1 or 100 μg/mL HDL). At the end of this chase period, the radioactivity in the medium and cells was determined by liquid scintillation counting, and the percent efflux was calculated as 100×(medium dpm)/(medium dpm+cell dpm). Percent efflux to acceptors was calculated as (percent efflux to acceptor)−(percent efflux to no acceptor). LNCaP treatment groups were compared to the mock treated sample using one way ANOVA with Dunnett's correction. Unpaired t test with Welch's correction was used to compare the T0901317-treated with the mock treated DU 145 cells.

Human Tissue Specimens

Prostate cancer tissues were obtained from patients treated with radical prostatectomy at Cleveland Clinic (Cleveland, Ohio). Benign prostate tissues were obtained from patients treated with radical cystoprostatectomy for either malignant or benign bladder disease at Cleveland Clinic (Cleveland, Ohio). All study specimens were collected under an approved Cleveland Clinic IRB protocol. All sections were retrieved and reviewed by dedicated genitourinary pathologists (C.M.G and S.M.F.) to confirm the original diagnosis. For MSP, formalin fixed paraffin embedded sections were de-paraffinized using xylene and rehydrated prior to genomic DNA extraction. About 2 µg genomic DNA from each sample was bisulfite treated using the EpiTect bisulfite conversion kit (Qiagen, Hilden, Germany) in 3 independent experiments. Only samples that show consistent methylation in all 3 experiments were deemed to harbor ABCA1 promoter methylation. Immunohistochemistry was performed on 4 µm sections. Antigen retrieval was performed prior to incubation with a custom anti-ABCA1 rabbit polyclonal antibody raised against AA 104-125 in NP_005493.2 (Thermo, Rockford, Ill.), OmniMap secondary antibody (Ventana, Tucson, Ariz.), and ChromoMap DAB (Ventana, Tucson, Ariz.). ABCA1 staining patterns were evaluated by C.M.G. and S.M.F. The specificity of this custom antibody was tested using both Western blotting and immunohistochemistry staining of DU 145 and LNCaP cells, as shown in FIG. 1. Scoring of ABCA1 staining was performed using the H-score system with the scale set from 0 to 3. McCarty et al., Cancer Res. 46(8 Suppl):4244s-8s (1986). H-score comparisons were performed using the Mann-Whitney U-test and Kruskal-Wallis test, with $p<0.05$ considered to be statistically significant. ABCA1 staining was independently analyzed by comparing the percentage of cancer cells stained positively for ABCA1 using the Kruskal-Wallis test, with $p<0.05$ considered to be statistically significant.

Results

Figure 2:
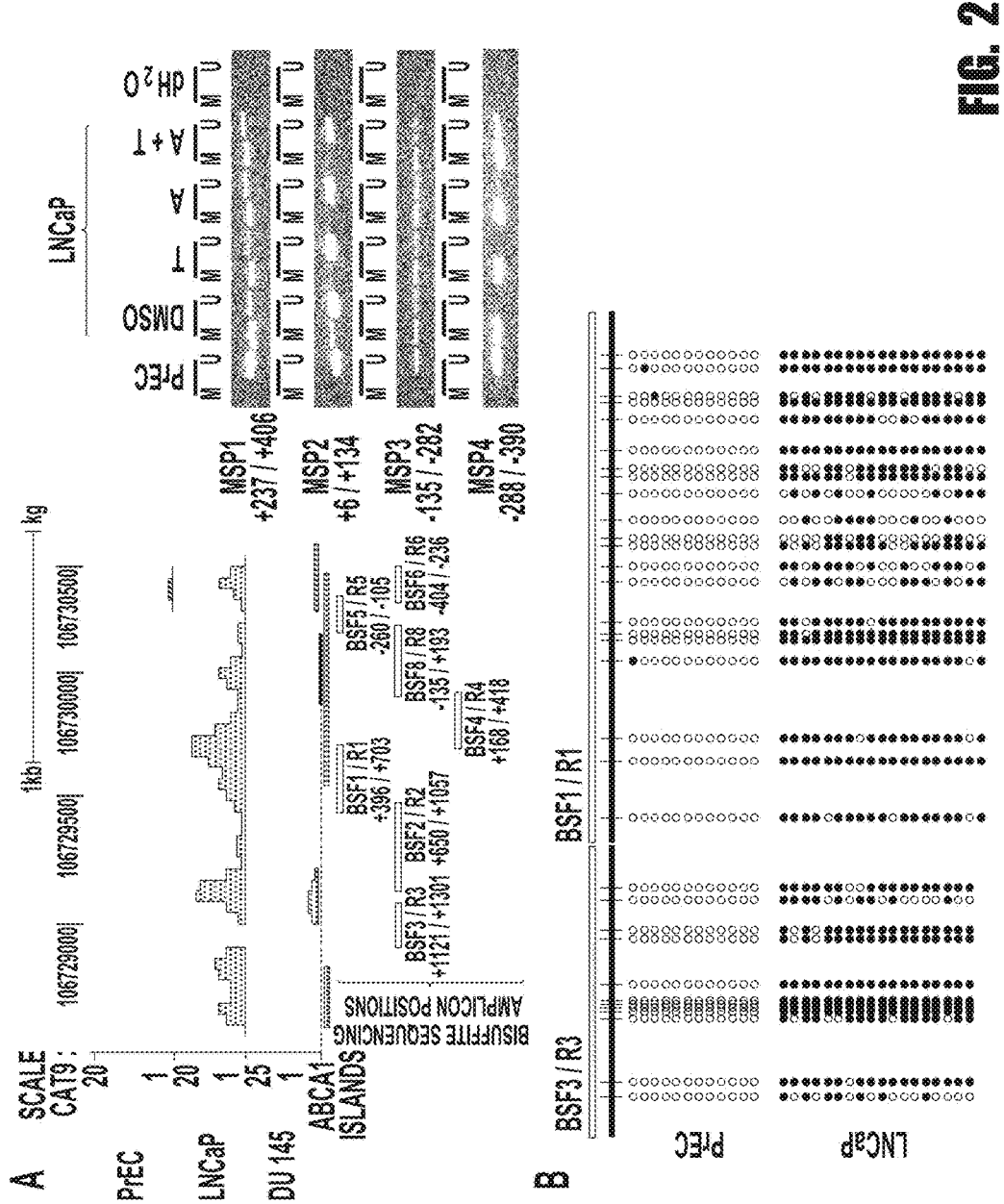
FIG. 2 provides graphs and images showing the results of DNA methylation analysis of ABCA1 5' regulatory sequences in prostate cell lines. (A) UCSC genome browser snapshot displaying the DNA methylation sequencing signals in PrEC, LNCaP, and DU 145 cells at the ABCA1 promoter region (UCSC Hg18, chr9:106, 728, 482-106, 730, 800). (B) Bisulfite sequencing validation in PrEC and LNCaP cells. Black circles represent methylated CpG sites, and white circles represent unmethylated CpG sites. (C) Methylation-specific PCR (MSP) results in PrEC and LNCaP cells either mock treated (DMSO), or treated with 10 µM T0901317 for 24 hours (T), 5 µM 5-aza-2'-deoxycytidine for 7 days (A), or a combination of 5-aza-2'-deoxycytidine and T0901317 (A+T).

DNA methylome profiles were assembled for normal prostate epithelial cells, PrEC, and prostate cancer cell lines, LNCaP and DU 145, using MiGS. Unambiguously mapped sequencing reads were used for generating the individual DNA methylome profiles. At a false discovery rate of 5%, we identified the major cellular cholesterol efflux transporter, ABCA1, to be densely methylated in its 5' regulatory region in LNCaP cells but not in PrEC or DU 145 cells (FIG. 2A).

While the ABCA1 promoter region is one of several thousand novel differentially methylated loci among the three prostate cell lines, the inventors focused on this gene because of its central role in intracellular cholesterol homeostasis. They verified this differential DNA methylation at the ABCA1 promoter by targeted bisulfite (BSF) sequencing in PrEC and LNCaP cells (FIG. 2B). This region was also assayed using methylation-specific PCR (MSP) (FIG. 2C). Both BSF sequencing and MSP results corroborated the robust DNA methylation at the ABCA1 promoter in LNCaP cells as detected by MiGS.

Figure 3:
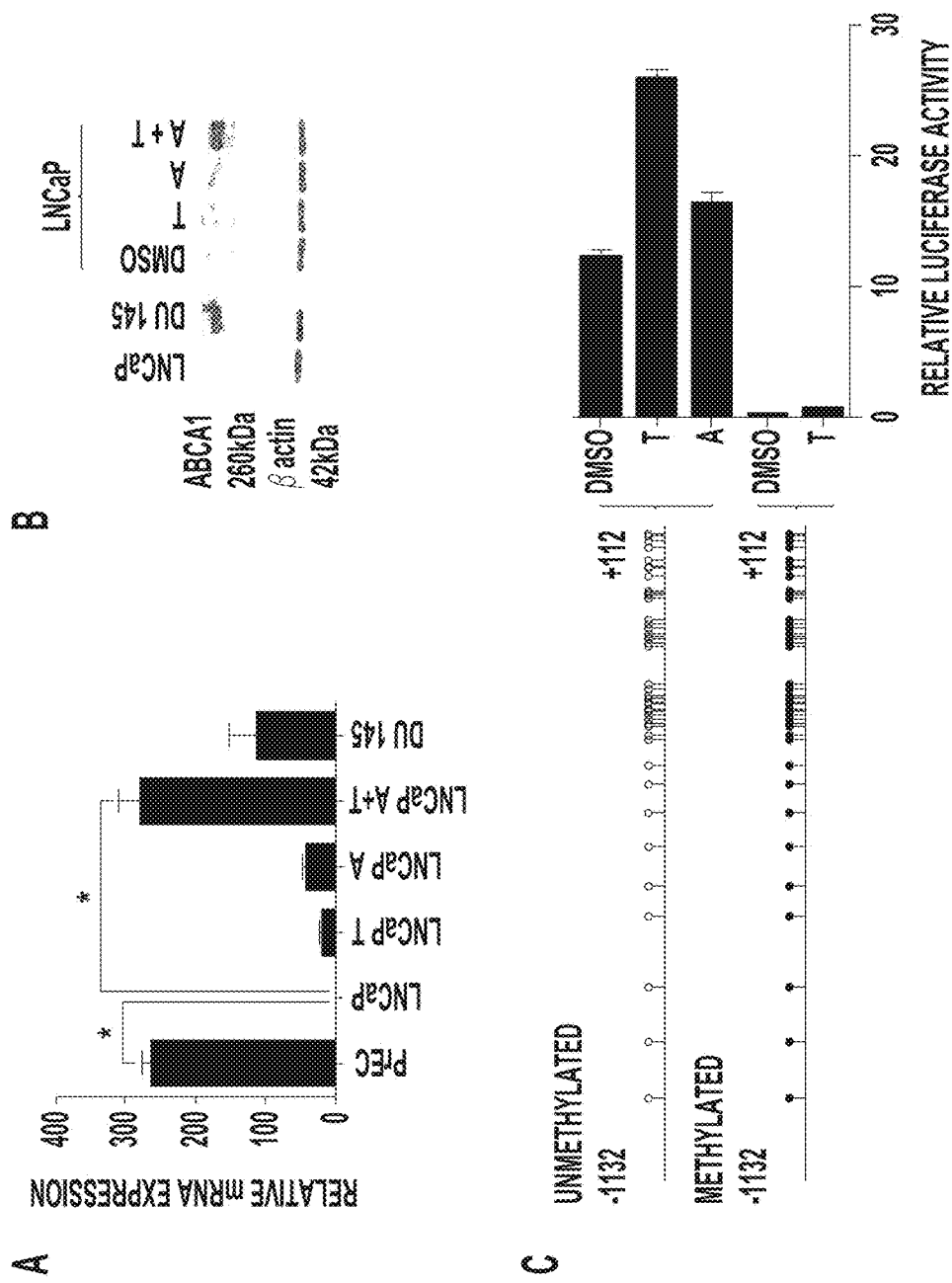
FIG. 3 provides graphs and images showing the effects of promoter DNA methylation on basal expression and inducibility of ABCA1. (A) Relative mRNA expression of ABCA1 in prostate cells. LNCaP cells were treated identically as in FIG. 2. Data are represented as mean±SEM from triplicate experiments and * indicates p<0.05. (B) Western blot analysis of ABCA1 and β actin (ACTB) in LNCaP and DU 145 cells. LNCaP cells were treated identically as in FIG. 2. (C) Luciferase reporter assay of the unmethylated and the methylated ABCA1 promoter in DU 145 cells. The cells containing the indicated reporter construct were either mock treated (DMSO) or treated with 10 µM T0901317 (T) or 5 µM 5-aza-2'-deoxycytidine (A) for 24 hours. Data are represented as mean±SEM from triplicate experiments. All pair-wise comparisons were statistically significant (p<0.05) except for between the two methylated treatment groups.

To examine the functional consequence of ABCA1 promoter methylation, RT-PCR was used to quantify ABCA1 mRNA expression in PrEC, LNCaP, and DU 145 cells (FIG. 3A). Compared with LNCaP cells, ABCA1 mRNA levels are at least 100-fold higher in PrEC and DU 145 cells where the ABCA1 promoter is not DNA methylated. This finding is consistent with transcriptional repression caused by ABCA1 promoter hypermethylation in LNCaP cells. LNCaP cells were treated with T0901317, a synthetic liver-x-receptor (LXR) α agonist known to induce ABCA1 transcription, and it was found that ABCA1 transcription was only modestly induced above baseline. Treatment of LNCaP cells with 5-aza-2'-deoxycytidine (5-aza), a demethylating agent, also did not strongly induce ABCA1 transcription. However, when the ABCA1 promoter in LNCaP is first demethylated with 5-aza, treatment with T0901317 resulted in robust activation of ABCA1 transcription to levels comparable to PrEC cells. The inventors confirmed demethylation of ABCA1 promoter by 5-aza using MSP (FIG. 2C). These data demonstrate that ABCA1 promoter hypermethylation renders it unresponsive to trans-activation. Not surprisingly, the lack of messenger RNA corresponds to a lack of ABCA1 protein expression in LNCaP cells while DU 145 cells clearly express ABCA1 (FIG. 3B). Again, demethylation of the ABCA1 promoter with 5-aza followed by treatment with T0901317 resulted in robust ABCA1 protein expression in LNCaP. It is worth noting that minimal ABCA1 expression and severely limited induction by trans-activators in LNCaP cells have been independently reported by other groups without a mechanistic explanation. Pommier et al., Oncogene. 29(18):2712-23 (2010); Leon et al., Prostate. 70(4): 390-400 (2010).

The effect of ABCA1 promoter hypermethylation on transcriptional activity (FIG. 3C) was then ascertained. An ABCA1 promoter/luciferase reporter construct was generated with sequences surrounding the ABCA1 transcription start site. A fully methylated version was produced by treating the ABCA1 promoter fragment with Sss I methylase and ligating it into the luciferase reporter construct prior to transfection. These vectors were transfected into DU 145 cells, which have the ability to express endogenous ABCA1. The unmethylated promoter expressed the luciferase reporter, and as expected, treatment with T0901317 resulted in a significant induction of reporter expression. Conversely, reporter activity from the methylated ABCA1 promoter was almost undetectable, and it was not induced by T0901317. These data show that promoter hypermethylation of ABCA1 is directly responsible for transcriptional repression and loss of responsiveness to activation by LXR agonist.

Figure 4:
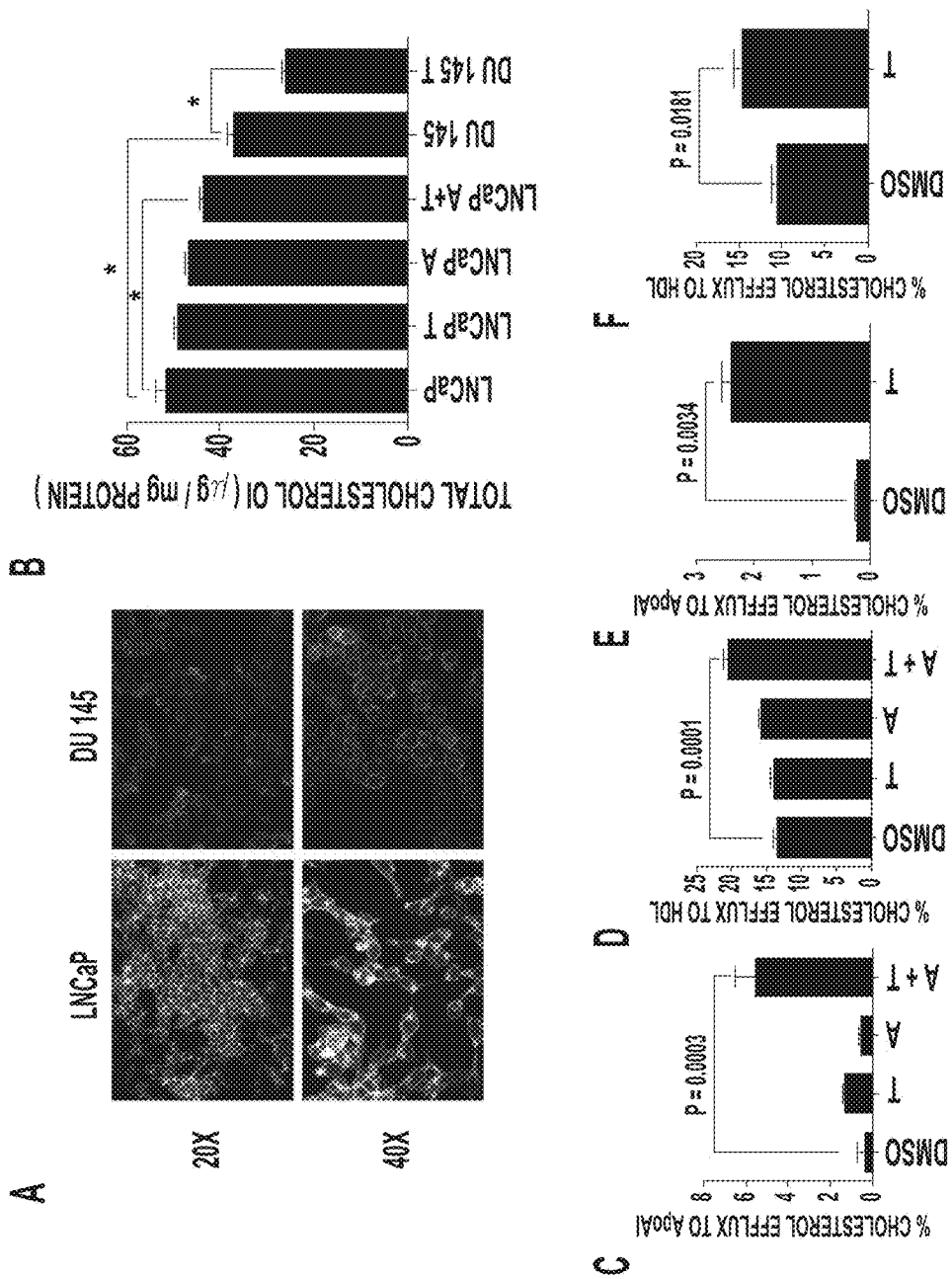
FIG. 4 provides graphs and images showing the results of the functional analysis of ABCA1 expression in prostate cancer cells. (A) Representative fields of filipin staining for LNCaP and DU145. (B) Total cellular cholesterol content for LNCaP and DU 145 cells. LNCaP cells were treated identically as in FIG. 2 while DU 145 cells were either mock treated (DMSO) or treated with 10 µM T0901317. (C-F) Cellular cholesterol efflux to APOA1 and HDL in LNCaP (C and D respectively) and DU 145 (E and F respectively) cells. Data are represented as mean±SEM from triplicate experiments, and * indicates p<0.05.

The functional consequence of ABCA1 promoter hypermethylation and transcriptional silencing was then examined. LNCaP and DU 145 cells were subjected to filipin staining, which allows visualization of free cholesterol, the major unesterified sterol in mammalian cells (FIG. 4A). Fluorescent microscopy showed that LNCaP cells have significantly elevated basal intracellular cholesterol levels when compared with DU 145. Total cellular cholesterol content was quantified biochemically (FIG. 4B), which confirmed that LNCaP has a higher basal level of intracellular cholesterol than DU 145 (51.2±4.4 µg/mg protein vs. 36.7±3.0 µg/mg protein). When LNCaP was treated with either T0901317 or 5-aza alone, intracellular cholesterol did not decrease significantly. However, when LNCaP was treated with 5-aza prior to T0901317, intracellular cholesterol was significantly lower than untreated LNCaP cells (43.6±1.4 µg/mg protein vs. 51.2±4.4 µg/mg protein). As expected, treatment of DU 145 with only T0901317 resulted in decreased intracellular cholesterol. Whether ABCA1 reactivation in LNCaP was responsible for the decrease in intracellular cholesterol content (FIGS. 4C and D) was then assessed. Cholesterol efflux to apolipoprotein A-I (APOA1), which can accept cellular cholesterol only via ABCA1, and to HDL, which can accept cholesterol from both ABCA1 and other transporters such as SR-B1 and ABCG1, was measured. Using APOA1 as an acceptor, treatment of LNCaP with either T0901317 or 5-aza did not result in robust increases in cholesterol efflux. However, treatment with 5-aza followed by T0901317 led to a 2.5-fold increase in cholesterol efflux to APOA1. When HDL was used as an acceptor, the same overall trend was observed in cholesterol efflux in LNCaP after treatment with T0901317, 5-aza-, or the two drugs combined. However, the magnitude of increase in cholesterol efflux after treatment with 5-aza followed by T0901317 was significantly lower when compared with APOA1 as an acceptor. These data suggest that the decrease in cholesterol after treatment of LNCaP with 5-aza followed by T0901317 is mainly due to re-activation of ABCA1. Conversely, treatment of DU 145 with T0901317 alone led to a significant increase in cholesterol efflux to APOA1, suggesting that ABCA1 was readily inducible in the absence of promoter methylation (FIGS. 4E and F). Treatment of DU 145 with T0901317 also resulted in a small, but statistically significant increase in cholesterol efflux to HDL.

Since ABCG1 is the other major contributor of cellular cholesterol efflux, ABCG1 promoter methylation and expression in these cells was also examined. By MiGS analysis, the ABCG1 promoter is free of DNA methylation in PrEC, LNCaP, and DU 145 cells. All three cell lines expressed ABCG1 mRNA robustly with no statistically significant differences among them while ABCA1 expression showed previously validated differences by microarray analysis, shown in Table 2. Altogether, these data support the notion that hypermethylation and consequent loss of expression of ABCA1 in LNCaP cells contribute to the aberrant accumulation of intracellular cholesterol in these cancer cells.

TABLE 2

ABCG1 and ABCA1 gene expression

| Comparison | ABCG1 | | ABCA1 | |
| --- | --- | --- | --- | --- |
| | Fold change | Adjusted p-value | Fold change | Adjusted p-value |
| LNCaP vs. PrEC | 1.0157 | 0.850 | 0.1220 | 0 |
| DU 145 vs. PrEC | 0.9966 | 0.971 | 0.5332 | 0.004 |
| DU 145 vs. LNCaP | 0.9811 | 0.802 | 4.3692 | 0 |

Figure 5:
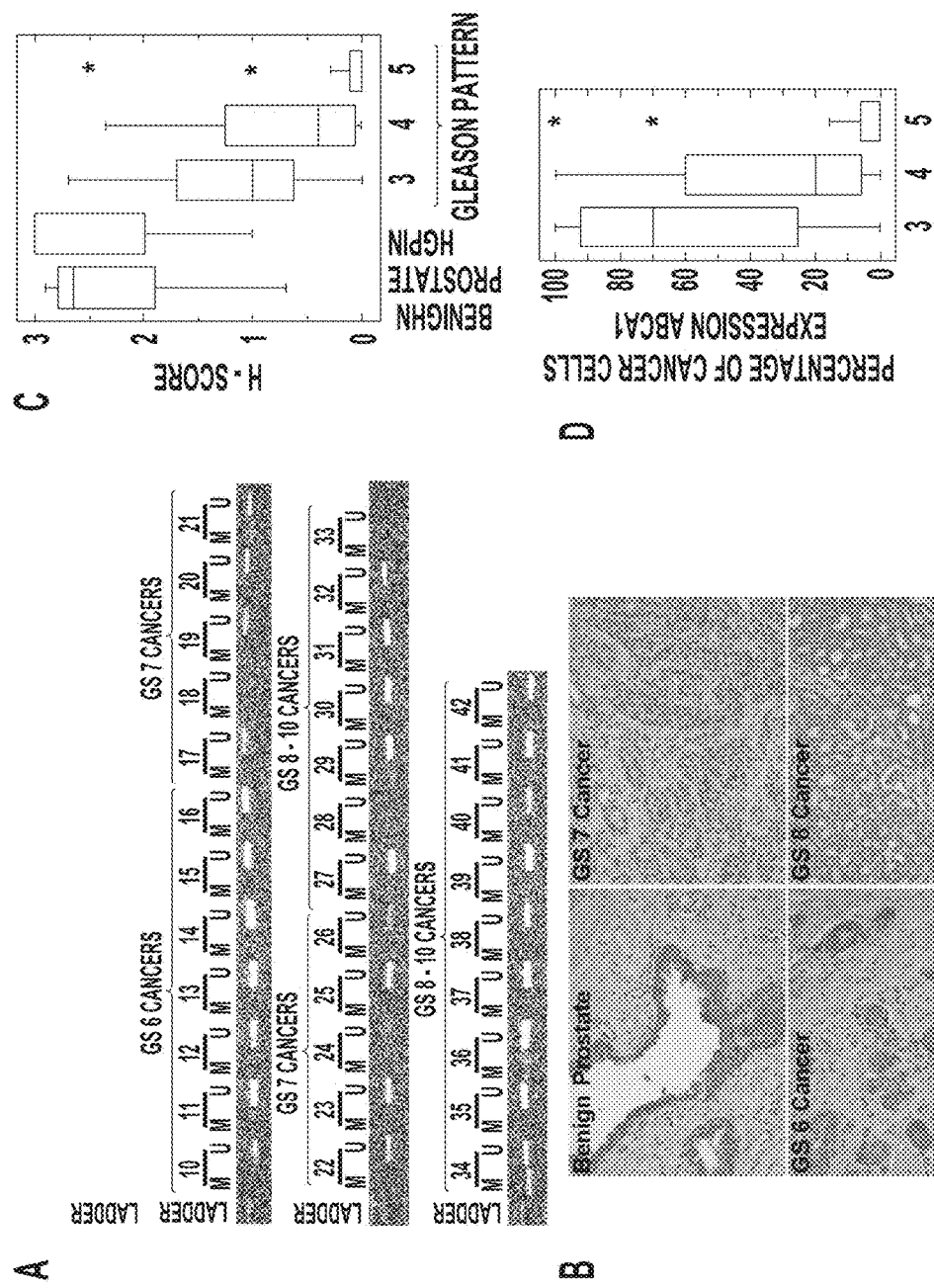
FIG. 5 provides graphs and images showing the results of the analysis of ABCA1 promoter methylation and expression in radical prostatectomy specimens. (A) Methylation-specific PCR (MSP) was performed using MSP1 primer set on bisulfite converted genomic DNA extracted from benign prostates (1-9), GS 6 (10-16), GS 7 (17-26), and GS 8-10 (27-42) prostate cancer specimens. LNCaP DNA was included as a positive control. Samples 18, 28, and 33 did not yield sufficient bisulfite converted DNA to produce successful PCR results and therefore were excluded from further analysis. (B) ABCA1 immunohistochemistry on benign prostate, GS 6, GS 7, and GS 8 prostate cancers. (C) Box plots of H-scores for ABCA1 staining in benign prostatic tissues (n=8), high grade prostatic intraepithelial neoplasia (HGPIN) (n=27), Gleason pattern 3 (n=13), 4 (n=24), and 5 (n=14) tumors. The box shows the first quartile, median, and third quartile values. The whiskers show the minimum and maximum values. For Gleason pattern 5, outlier values, defined as three times the interquartile range, are present, and the whiskers denote 1.5 times the interquartile range with outliers plotted as individual black circles. The difference among the H-scores of Gleason patterns 3, 4, and 5 is statistically significant (p=0.0017; Kruskal-Wallis test). (D) Box plots of percentages of cancer cells expressing ABCA1. Graphical representation is identical to FIG. 5c. The difference among the percentages of cells staining positive for ABCA1 in Gleason patterns 3, 4, and 5 is statistically significant (p=0.0013; Kruskal-Wallis test).

To assess the prevalence of ABCA1 hypermethylation in human prostate cancer, MSP was performed on DNA extracted from 9 benign prostatic tissue samples from cystoprostatectomy specimens and 33 prostate cancers. Of the 33 prostate cancer samples, 30 yielded high quality bisulfite converted DNA for this analysis. ABCA1 hypermethylation was not found in any of the benign prostatic tissue samples; however, 4 of 30 prostate cancers (samples 21, 29, 34, and 36) showed ABCA1 hypermethylation (FIG. 5A). Notably, ABCA1 hypermethylation was only seen in men with intermediate and high risk prostate cancer (1/6 of Gleason score (GS) 7 cancers and 3/14 of GS 8-10 cancers). Biochemical recurrence after radical therapy was documented in all of these men. Furthermore, the expression of ABCA1 in prostate tissue was investigated by developing a custom antibody to the protein and performing immunohistochemistry on individual radical prostatectomy specimens and tissue microarrays containing prostate cancers (FIG. 5B). In a subsequent study, 387 subjects were stained with the custom ABCA1 polyclonal antibody. Of these, 350 subjects were informative for ABCA1 expression. ABCA1 expression is inversely correlated with total Gleason score (OR=−0.067, adjusted p-value=0.006) and the primary Gleason pattern in this cohort (OR=−0.037, adjusted p-value=0.017).

The H-score method was used to evaluate the ABCA1 expression in a semiquantitative fashion. There was significant heterogeneity of ABCA1 staining in each cancer specimen due to differences in tumor pattern. Thus, the inventors determined the H-score of each of the following patterns observed: benign prostatic tissues (n=8), high grade prostatic intraepithelial neoplasia (HGPIN) (n=27), and Gleason patterns 3 (n=13), 4 (n=24), and 5 (n=14) (FIG. 5C). No significant difference was observed in ABCA1 expression between benign prostatic tissues and HGPIN (median H-score 2.65 vs. 3.00). ABCA1 expression was significantly lower for prostate cancers when compared with benign prostatic tissues (median H-score 0.35 vs. 3.00; p<0.001; Mann-Whitney test). Moreover, there was an inverse correlation between ABCA1 expression and Gleason pattern. Both Gleason pattern 4 and 5 cancers had a lower median H-score when compared with Gleason pattern 3 cancer (0.40 and 0.00 vs. 1.00; p=0.0017; Kruskal-Wallis test), and 71% of Gleason pattern 5 cancers completely lost ABCA1 expression. When the percentage of cancer cells staining positively for ABCA1 was examined, a statistically significant difference (p=0.0013; Kruskal-Wallis test) among the Gleason patterns (FIG. 5D) was observed. Specifically, ranking by the percentage of cells expressing ABCA1, Gleason pattern 3 was the highest, Gleason pattern 4 was second, and Gleason pattern 5 was the lowest (median percentages 70%, 20%, and 0% respectively). These results demonstrate that ABCA1 hypermethylation is specific to prostate cancer, and decrease in ABCA1 expression is associated with tumor aggressiveness.

Discussion

After compiling the methylomes for the three prostate cell lines, the inventors initially focused on candidates involved in cholesterol homeostasis. As discussed previously, cholesterol has two proposed roles in the development of advanced prostate cancer: serving as a substrate in de novo androgen synthesis in CRPC and enhancing AKT signaling by stabilizing lipid raft structure. However, the exact mechanism by which cholesterol accumulates inside the cancer cells is not clearly defined. The inventors have identified ABCA1 promoter hypermethylation and subsequent transcriptional silencing as one mechanism that prostate cancer cells can use to maintain elevated intracellular cholesterol levels. Since intracellular cholesterol level is the net sum of uptake, synthesis, and efflux, disruption of a major transporter involved in efflux will result in intracellular cholesterol accumulation. It was demonstrated that this is the case through fluorescence microscopy as well as cholesterol quantification. When mechanisms responsible for cholesterol homeostasis are intact, excess cholesterol is converted to oxysterols which bind to LXR's so that ABCA1 transcription is activated. Schmitz G, Langmann T., Biochim Biophys Acta., 1735(1):1-19 (2005). The inventors showed that in LNCaP cells, ABCA1 promoter hypermethylation prevents ABCA1 activation by the synthetic LXR agonist, T0901317, and demethylation of the promoter by 5-aza restores responsiveness to T0901317. As a result, cholesterol levels are significantly decreased when compared with untreated LNCaP cells or those treated with either agent alone.

When human prostate tissue was examined, it was found that ABCA1 promoter hypermethylation was seen in prostate cancer but not benign prostatic tissue. Interestingly, this epigenetic alteration has a higher prevalence in intermediate and high grade cancers when compared with low grade cancers. Importantly, immunohistochemistry revealed that loss of ABCA1 expression is more prevalent in higher grade tumors than can be explained by promoter hypermethylation alone. These data suggest that ABCA1 inactivation may be important in the development of or progression to aggressive and/or advanced prostate cancer. Identifying the exact mechanism underlying ABCA1 inactivation is important, since promoter hypermethylation will render the gene unresponsive to LXR agonists but other mechanisms may not. Although it is presumed that statins protect against aggressive and advanced prostate cancers by inhibiting cholesterol synthesis, it would be interesting to see whether their use would be successful in prostate cancers with ABCA1 inactivation.

In summary, ABCA1 promoter hypermethylation and gene inactivation leads to the accumulation of cholesterol in prostate cancer cells. Thus, this cellular cholesterol efflux pathway may be an important determinant of prostate cancer aggressiveness and a potential therapeutic target.

The complete disclosure of all patents, patent applications, and publications, and electronically available material cited herein are incorporated by reference. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

What is claimed is:

1. A method of diagnosing prostate cancer in a subject, comprising:
    (a) obtaining a urine or prostate sample from the subject;
    (b) detecting the level of expression of ABCA1 protein in the sample by contacting the sample with a polyclonal antibody that is specific for the ABCA1 protein and generated using, and binds to, the ABCA1 antigen sequence CRLFSDARRLLLYSQKDTSMKDM (SEQ ID NO:1), and detecting the level of antibody binding by immunohistochemical staining; and
    (c) comparing the level of expression of ABCA1 in the sample to the level of a control sample, wherein a decreased level of ABCA1 protein compared to the control indicates the subject has prostate cancer.

2. The method of claim 1, wherein the sample is a prostate sample.

* * * * *